(12) United States Patent
Rothstein et al.

(10) Patent No.: US 7,014,998 B2
(45) Date of Patent: Mar. 21, 2006

(54) SCREENING IMMUNOMODULATORY AGENTS BY CTLA-4 UPREGULATION

(75) Inventors: David M. Rothstein, Guilford, CT (US); Giacomo P. Basadonna, Guilford, CT (US)

(73) Assignee: Yale University, New Haven, CT (US)

( * ) Notice: Subject to any disclaimer, the term of this patent is extended or adjusted under 35 U.S.C. 154(b) by 221 days.

(21) Appl. No.: 09/961,503

(22) Filed: Sep. 24, 2001

(65) Prior Publication Data

US 2002/0041849 A1 Apr. 11, 2002

Related U.S. Application Data

(60) Provisional application No. 60/237,359, filed on Sep. 30, 2000.

(51) Int. Cl.
*C12N 15/00* (2006.01)

(52) U.S. Cl. .................. 435/6; 435/7.24; 435/40.5; 424/9.1

(58) Field of Classification Search ................ 435/6, 435/40.5, 7.1, 325, 7.24; 424/9.1; 436/501, 436/63
See application file for complete search history.

(56) References Cited

U.S. PATENT DOCUMENTS

| | | | |
|---|---|---|---|
| 5,434,131 A | * | 7/1995 | Linsley et al. |
| 6,024,957 A | | 2/2000 | Lazarovits et al. |
| 6,084,067 A | * | 7/2000 | Freeman et al. |
| 6,099,838 A | | 8/2000 | Lazarovits et al. |
| 6,106,834 A | | 8/2000 | Lazarovits et al. |

OTHER PUBLICATIONS

Xia et al., CMLS Cell. Mul. Life. Sci. 55:1649–56, 1999.*
Curreno et al, Journal of Immunology 165:1352–1356, 2000.*
Harper et al. (J Immunol 1991 vol. 147(3) pp. 1037–1044).*
Fecteau, S., et al., Nature Immunology 2: 58–63 (2001).
Rothstein, D., et al., J. ASN abstract (2000) "A New Paradigm for the Induction of Tolerance".
Rothstein, D., et al., J. ASN abstract (2000) "Tolerance Induced Through Alteration of Signal One . . . ".
Rothstein, D., and Basadonna, G., Graft 2: issue 6 immunosuppression review, Nov./Dec. 199: "Anti–CD45".
Rothstein, D., et al., Journal of Immunology 166: 322–329 (2001).
Tian, J., et al., J. ASN abstract (2001) "CD–45 Mediation Upregulation of the CTLA–4 Inhibitory Receptor . . . ".
Tivol, E. et al. Loss of CTLA–4 leads to massive lymphoproliferation and fatal multiorgan tissue destruction, revealing a critical negative regulatory role of CTLA–4. Immunity 3, 541–547 (1995).
Waterhouse P., Penninger, J. M., Timms E., Wakeham A., Shahinian A., Lee K. P., Thompson C. B., Griesser, H., & Mak T. W. Lymphoproliferative disorders with early lethality in mice deficient in Ctla–4. Science 270, 985–988 (1995).
Perez, V. L. et al. Induction of peripheral T cell tolerance in vivo requires CTLA–4 engagement. Immunity 6, 411–417 (1997).
Leach, D. R., Krummel, M. F. & Allison, J. P. Enhancement of antitumor immunity by CTLA–4 blockade. Science 271. 1734–1736 (1996).
Luhder, F., Hoglund, P., Allison, J. P., Benoist, C. & Mathis, D. Cytotoxic T lymphocyte–associated antigen 4 (CTLA–4) regulates the unfolding of autoimmune diabetes. J. Exp. Med. 187, 427–432 (1998).
Karandikar, N. J., Vanderlugt, C. L., Walunas, T. L., Miller, S. D. & Bluestone, J. A. CTLA–4: A negative regulator of autoimmune disease. J. Exp. Med. 184, 783–788 (1996).
Takahashi, T. et al. Immunologic self–tolerance maintained by CD25(+)CD4(+) regulatory T cells constitutively expressing cytotoxic T lymphocyte–associated antigen 4. J. Exp. Med. 192, 303–310 (2000).
Judge, T. A. et al. The role of CD80, CD86, and CTLA4 in alloimmune responses and the induction of long–term allograft survival. J. Immunol. 162, 1947–1951 (1999).
Linsley, P. S. et al. Intracellular trafficking of CTLA–4 and focal localization towards sites of TCR engagement. Immunity 4, 535–543 (1996).
Alegre, M. L. et al. Regulation of surface and intracellular expression of CTLA4 on mouse T cells. J. Immunol. 157, 4762–4770 (1996).
Finn, P. W. et al. Synergistic induction of CTLA–4 expression by constimulation with TCR plus CD28 signals mediated by increased transcrption and messenger ribonucleic acid stability. J. Immunol. 158, 4074–4081 (1997).
Krummel, M. F. & Allison, J. P. CD28 and CTLA–4 have opposing effects on the response of T cells to stimulation. J. Exp. Med. 182, 459–465 (1995).
Walunas, T. L. et al. CTLA–4 can function as a negative regulator of T cell activation. Immunity 1, 405–413 (1994).
Trowbridge, I. S. & Thomas, M. L. CD45: An emerging role as a protein tyrosine phosphatase required for lymphocyte activation and development. Ann. Rev. Immunol. 12, 85–116 (1994).

(Continued)

*Primary Examiner*—Patricia A. Duffy
(74) *Attorney, Agent, or Firm*—Carmody & Torrance LLP

(57) ABSTRACT

Screens that directly or indirectly measure or qualitatively observe CTLA-4 expression or function by animals or cell cultures, or that indirectly measure dependence of an agent on CTLA-4 by comparison to animals or cell cultures that lack CTLA-4, identify agents that are useful in immunosuppression and the generation of immunologic tolerance for the prevention and treatment of transplant rejection, autoimmune and inflammatory diseases.

12 Claims, 9 Drawing Sheets

OTHER PUBLICATIONS

Kashio, N., Matsumoto, W., Parker, S. & Rothstein, D. M. The second domain of the CD45 transmembrane protein tyrosine phosphatase is critical for IL2 secretion and for recruitment of substrates in vivo. J. Biol. Chem. 273, 33856–33863 (1998).

Bottomly, K. et al. A monoclonal antibody to murine CD45R distinguishes CD4 T cell populations that produce different cytokines. Eur. J. Immunol. 19, 617–623 (1989).

Lee, W., Yin, X.-M. & Vitetta, E. Functional and ontogenetic analysis of murine $CD45^{hi}$ and $CD45^{lo}$ $CD4^+$ T cells. J. Immunol. 144, 3288–3295 (1990).

Powrie, F. et al. Inhibition of Th1 response prevents inflammatory bowel disease in scid mice reconstituted with $CD45RB^{hi}$ $CD4^+$T cells. Immunity 1, 553–562 (1994).

Morimoto, C., Letvin, N. L., Distaso, J. A., Aldrich.W. R. & Schlossman, S. F. The isolation and characterization of the human suppressor inducer T cell subset. J. Immunol. 134, 1508–1515 (1985).

Rothstein, D. M., Yamada, A., Schlossman, S. F. & Morimoto, C. Cyclic regulation of CD45 isoform expression in a long–term human $CD4^+CD45RA^+$ T cell line. J. Immunol. 146, 1175–1183 (1991).

Sparshott, S. & Bell, E. Membrane CD45R isoform exchange on CD4 T cells is rapid, frequent and dynamic in vivo. Eur. J.Immunol. 24, 2573–2578 (1994).

Michie, C. A., McLean, A., Alcock, C. & Beverly, P. C. L. Lifespan of human lymphocyte subsets defined by CD45 isoforms. Nature 360, 264–265 (1992).

McKenney, D. W., Onodera, H., Gorman, L., Mimura, T. & Rothstein, D. M. Individual isoforms of the CD45 protein tyrosine phosphatase differentially regulate interleukin 2 secretion and activation signal pathways involving Vav in T cells. J. Biol. Chem. 270, 24949–24954 (1995).

Onodera, H., Motto, D.G., Koretzky, G. A. & Rothstein, D. M. Differential Regulation of Activation–Induced Tyrosine Phosphorylation and Recruitment of SLP–76 to Vav by Distinct Isoforms of the CD45 Protein Tyrosine Phosphatase. J. Biol. Chem. 271, 2225–2230 (1996).

Novak, T. et al. Isoforms of the transmembrane tyrosine phosphatase CD45 differentially affect T cell recognition. Immunity 1, 109–119 (1994).

Basadonna, G. et al. Antibody mediated targeting of CD45 isoforms: A novel immunotherapeutic strategy. Proc. Nat. Acad. Sci. USA. 95, 3821–3826 (1998).

Lazárovits, A. et al. Prevention and reversal of renal allograft rejection by antibody against CD45RB. Nature 380, 717–720 (1996).

Metz, D. P., Farber, D. L., Taylor, T. & Bottomly, K. Differential role of CTLA–4 in regulation of resting memory versus naive CD4 T cell activation. J. Immunol. 161, 5855–5861 (1998).

Chuang, E. et al. Interaction of CTLA–4 with the clathrin–associated protein AP50 results in ligand–independent endocytosis that limits cell surface expression. J. Immunol. 159, 144–151 (1997).

Croft, M., Duncan, D. D. & Swain, S. L. Response of naive antigen–specific $CD4^+$ T cells in vitro: characteristics and antigen–presenting cell requirements. J. Exp. Med. 176, 1431–1437 (1992).

Liu, J. et al, Calcineurin is a common target of cyclophilin–cyclosporin A and FKBP–FK506 complexes. Cell 66, 807–815 (1991).

Walunas, T. L. & Bluestone, J. A. CTLA–4 regulates tolerance induction and T cell differentiation in vivo. J. Immunol. 160, 3855–3860 (1998).

Read, S., Malmstrom, V. & Powrie, F. Cytotoxic T lymphocyte–associated antigen 4 plays an essential role in the function of $CD25^+CD4^+$ regulatory cells that control intestinal inflammation. J. Exp. Med. 192, 295–302 (2000).

Salomon, B. et al. B7/CD28 constimulation is essential for the homeostasis of the $CD4^+CD25^+$immunoregulatory T cells that control autoimmune diabetes. Immunity 12, 431–440 (2000).

Perkins, D. et al. Regulation of CTLA–4 expression during T cell activation. J. Immunol. 156, 4154–4159 (1996).

Shiratori, T. et al. Tyrosine phosphorylation controls internalization of CTLA4 by regulating its interaction with clathrin–associated adaptor complex AP–2. Immunity 6, 583–589 (1997).

Schneider, H. et al. Cytolytic T lymphocyte–associated antigen–4 and the TCR /CD3 complex, but not CD28, interact with clathrin adaptor complexes AP–1 and AP–2. J. Immunol. 163, 1868–1879 (1999).

Rothstein, D. M., Saito, H., Streull, M., Schlossman, S. F. & Morimoto, C. The alternative splicing of the CD45 tyrosine phosphatase is controlled by negative regulatory trans–acting splicing factors. J. Biol. Chem. 267, 7139–7147 (1992).

Tedder, T. F., Clement, L. T. & Cooper, M. D. Human lymphocyte differentiation antigens HB–10 and HB–11 I. Ontogeny of antigen expression. J. Immunol. 134, 2983–2988 (1985).

Bell, E. B. & Sparshott, S. M. Interconversion of CD45R subsets of CD4 T cell in vivo. Nature 348, 163–166 (1990).

Leitenberg, D., Novak, T., Farber, D. L., Smith, B. R. & Bottomly, K. The extracellular domain of CD45 controls association with the CD4–T cell receptor complex and the response to antigen specific stimulation. J. Exp. Med. 183, 249–259 (1996).

Leitenberg, D., Constant, S., Lu, D. D., Smith, B. R. & Bottomly, K. CD4 and CD45 regulate qualitatively distinct patterns of calcium mobilization in individual $CD4^+$ T cells. Eur. J.Immunol. 25, 2445–2452 (1995).

Desai, D., Sap, J., Schiessinger, J. & Weiss, A. Ligand–mediated negative regulation of a chimeric transmembrane receptor tyrosine phosphatase. Cell 73, 541–554 (1993).

Li, Y. et al. Blocking both signal 1 and signal 2 of T–cell activation prevents apoptosis of alloreactive T cells and induction of peripheral allograft tolerance. Nat. Med. 5, 1298–1302 (1999).

\* cited by examiner

SCREENING IMMUNOMODULATORY AGENTS BY CTLA-4 UPREGULATION

CROSS-REFERENCES TO RELATED APPLICATIONS

This application claims priority benefit of U.S. Ser. No. 60/237,359, filed Sep. 30, 2000.

STATEMENT REGARDING FEDERALLY SPONSORED RESEARCH

This invention was made with partial government support under grants AI-36317 and AI-45485 from the National Institutes of Health. The government has certain rights in the invention.

BACKGROUND OF THE INVENTION

1. Field of the Invention

The present invention relates to methods of identifying agents that upregulate CTLA-4 that are useful in immuno-suppression and the generation of immunologic tolerance for the prevention and treatment of transplant rejection and autoimmune and inflammatory diseases.

2. Description of the Related Art

Transplantation is now the treatment of choice for end-stage heart, kidney, and liver disease. Although improved immuno-suppression has led to excellent short-term allograft survival, acute rejection still occurs and long-term results remain inadequate. Moreover, sub-clinical rejection is still relatively frequent on protocol biopsies and may contribute to chronic rejection. Finally, current therapy requires life-long immunosuppression with attendant risks of infection and malignancy. Therefore, there is a need to develop improved immunosuppressive agents that are both more effective and more specific for prevention of rejection (with less generalized immunosuppression and side-effects). The ideal therapy would consist of a finite course of treatment that would induce specific tolerance (lack of responsiveness) for the transplant, while leaving the immune system intact to defend against other threats. Achieving tolerance would reduce rejection, increase long-term engraftment, and eliminate continuous immunosuppression, thereby reducing morbidity, mortality, and cost.

Under normal circumstances, the immune system exhibits tolerance (i.e. lack of responsiveness) to self-antigens. Abnormalities in self-tolerance lead to immune responses against self and debilitating inflammatory disorders commonly called autoimmune diseases. These include rheumatoid arthritis, type I diabetes, systemic lupus erythematosis, inflammatory bowel disease (such as ulcerative colitis and Crohn's disease), myasthenia gravis, multiple sclerosis, vitiligo, pernicious anemia, among many others. As in the case of transplantation, current therapy has variable success and is fraught with risks of over-immunosuppression (malignancy, infection) and other side effects (cardiovascular disease, hypertension, diabetes). Once again, more effective immunomodulatory agents, particularly those able to restore immunologic tolerance, would be of great benefit.

The mechanisms underlying tolerance are complex and poorly understood, but it is clear that T lymphocytes, commonly called T cells, play a primary role in both allograft rejection and autoimmunity. T cell activation is not "all or none". Rather, the T cell response upon exposure to antigen can be modified, resulting in downregulation, anergy, or the development of regulatory cells which inhibit the activity of other T cells.

CTLA-4 (Cytotoxic T cell Antigen-4; CD 152) is a molecule expressed primarily by T lymphocytes that is critically involved in downregulation of the immune response and in the generation of tolerance (specific non-responsiveness) in transplantation and autoimmunity. CTLA-4 normally interacts with a ligand on antigen presenting cells called B7 (CD80 and CD86)—producing an inhibitory signal. Animals genetically deficient in CTLA-4 rapidly develop a uniformly fatal autoimmune syndrome. In normal animals, blockade of CTLA-4-mediated negative signaling with antibodies results in augmented immune responsiveness against tumors and prevents tolerance to transplanted organs, soluble antigens, and can precipitate de novo autoimmune disease. Such data indicate that augmentation of CTLA-4-derived negative signals would be of great help in promoting stable engraftment of transplanted tissues and in preventing/treating autoimmunity. Unfortunately there are no known agonist ligands to CTLA-4 that will act in soluble form. All known antibodies against CTLA-4 only block the CTLA-4 signal and actually augment immune responsiveness as noted above. Anti-CTLA-4 mAbs only give rise to inhibitory signals when they are extensively cross-linked (e.g., on plastic or rubber beads, or by co-administration of an another antibody that recognizes the anti-CTLA-4 (anti-globulin)). These are not practical approaches in vivo.

CTLA-4 expression is tightly controlled, however, and little is known about specific signals involved in upregulating its expression. Normally expression is upregulated only after a cell is fully activated and enters the cell cycle, reaching maximal levels 72 hours after ligation of the T cell receptor and CD28 costimulatory molecules. CTLA-4 expression is primarily intracellular. However, cell activation induces rapid cycling to the cell surface and back. How constitutive CTLA-4 expression (i.e., small amounts that are present prior to activation) is regulated is completely unknown. Recently it has become clear that cells that express even low levels of CTLA-4 may play a critical role as regulatory cells that down-regulate autoimmune responses (thereby preventing autoimmune disease). Such cells may also play an important role in preventing rejection and promoting transplant tolerance. However, until now there has been no known way to capitalize on this potent downregulatory pathway.

In summary, animals genetically deficient in CTLA-4 rapidly develop a uniformly fatal lymphoproliferative/autoimmune syndrome. In normal animals, blockade of CTLA-4-mediated negative signaling with antibodies, results in augmented immune responsiveness against tumors and prevents tolerance to transplanted organs or soluble antigens. Such data indicate that augmentation of CTLA-4-derived signals would be of great help in promoting stable engraftment of transplanted tissues and in preventing/treating autoimmunity. Unfortunately, at the present time, there are no candidate antibodies, soluble ligands, or small molecules that augment CTLA-4-mediated negative signals. Another approach, equally unfeasible until now, would be to specifically upregulate CTLA-4 expression, allowing for augmented CTLA-4-signaling through interaction with its physiological B7 ligands. It would be very useful to have screens to identify agents that act by either means to augment CTLA-4 signaling.

BRIEF SUMMARY OF THE INVENTION

It is a primary objective of the invention to provide screens that identify agents useful for the treatment or prevention of immune-mediated disease and/or rejection of allogeneic or xenogeneic cells, tissue, or organ transplants, by promoting immunosuppression or immunological tolerance in mammals.

This and other objectives are accomplished by the present invention which provides screens for identifying agents that immunomodulate by upregulating CTLA-4. Methods of the invention utilize different techniques to directly or indirectly measure or qualitatively observe CTLA-4 expression by animals or cell cultures, or to indirectly measure dependence of an agent on CTLA-4 by comparison to animals or cell cultures that lack CTLA-4. Regardless, all the screens measure or assess CTLA-4 upregulation or function.

In a typical direct measurement screen of the invention, useful agents are identified by administering test agents to animals or mammalian cells that express CTLA-4 in culture, and the cell surface and/or cytoplasmic levels of CTLA-4 are measured in biological samples taken from the animals or the cultures using immunoassays, protein determinations, and the like. Useful agents are identified by observation of increased levels of CTLA-4 in test samples in vivo or in vitro when compared with control samples.

Another type of screen employs anti-CTLA-4 antibodies that normally block CTLA-4 signaling. Test agents are administered with and without anti-CTLA-4 antibodies to an animal or to mammalian cells that express CTLA-4 in culture. Identification of agents useful in promoting immunosuppression or immunologic tolerance through CTLA-4 is achieved by observation that the anti-CTLA-4 antibody interfered with the ability of the test agent to block an in vivo immune response in the animal, or interfered with the activity of the agent in a functional assay such as cytokine production, cell proliferation, cytotoxicity, cell death, and the like when compared with in vivo or in vitro observations made in the absence of antibody.

In a third screen, CTLA-4 deficient animals or cells are employed instead of blocking CTLA-4 using anti-CTLA-4 antibodies. Test agents are compared in animals or cells that express CTLA-4 and similar animals or cells that lack CTLA-4 expression. In this case, the test agent is administered to animals, or added to cells in culture, which are then examined in clinical or functional assays in vivo or in vitro. The differences in functional or clinical response in vitro or in vivo are assessed and compared to controls having no test agent. Useful immunomodulating agents are identified by observation that lack of CTLA-4 expression interfered with the ability of the test agent to block an immune response, or interfered with a functional property of the agent.

Panel A: Surface CD45RB and intracellular CTLA-4 expression on CD4+ cells was determined by 3-color immunofluorescence analysis of splenocytes from untreated animals (left panels) or animals on day 6 after treatment with anti-CD45RB (right panels). After staining with anti-CD4-Cychrome 5 and anti-CD45RB-FITC, cells were permeabilized and stained with either anti-CTLA-4-PE (top panels) or control Hamster IgG-PE (bottom panels). After gating on CD4+ lymphocytes, green and red fluorescence were analyzed and are displayed on a log scale. Numbers within each histogram represent the percent of cells within each quadrant. Surface CTLA-4 expression (non-permeabilized cells) was essentially negative. Data are representative of at least 5 animals in each group.

Panel B: CTLA-4 and CD45RB expression on CD4 cells from untreated (upper row) vs. day 6 anti-CD45RB-treated (lower row) animals after activation-induced cycling of CTLA-4 between the cytoplasm and cell surface. Purified CD4 cells were stimulated with plate-bound anti-CD3 plus anti-CD28 for 4 h in the presence of Hamster-Ig-PE (I.C. Control) or anti-CTLA-4-PE (I.C. CTLA-4). After incubation cells were stained with anti-CD45RB-FITC and analyzed by flow cytometry. Surface expression was determined by exposing CD4 cells to Hamster-Ig-PE or anti-CTLA-4-PE (Surface Control and Surface CTLA-4) only after removal from plate-bound stimulation. Numbers represent the percent of cells within each quadrant. Data are representative of 3 experiments. Cells cultured with anti-CTLA-4-PE in wells lacking anti-CD3 and anti-CD28, exhibited only surface levels of CTLA-4.

Figure 3:
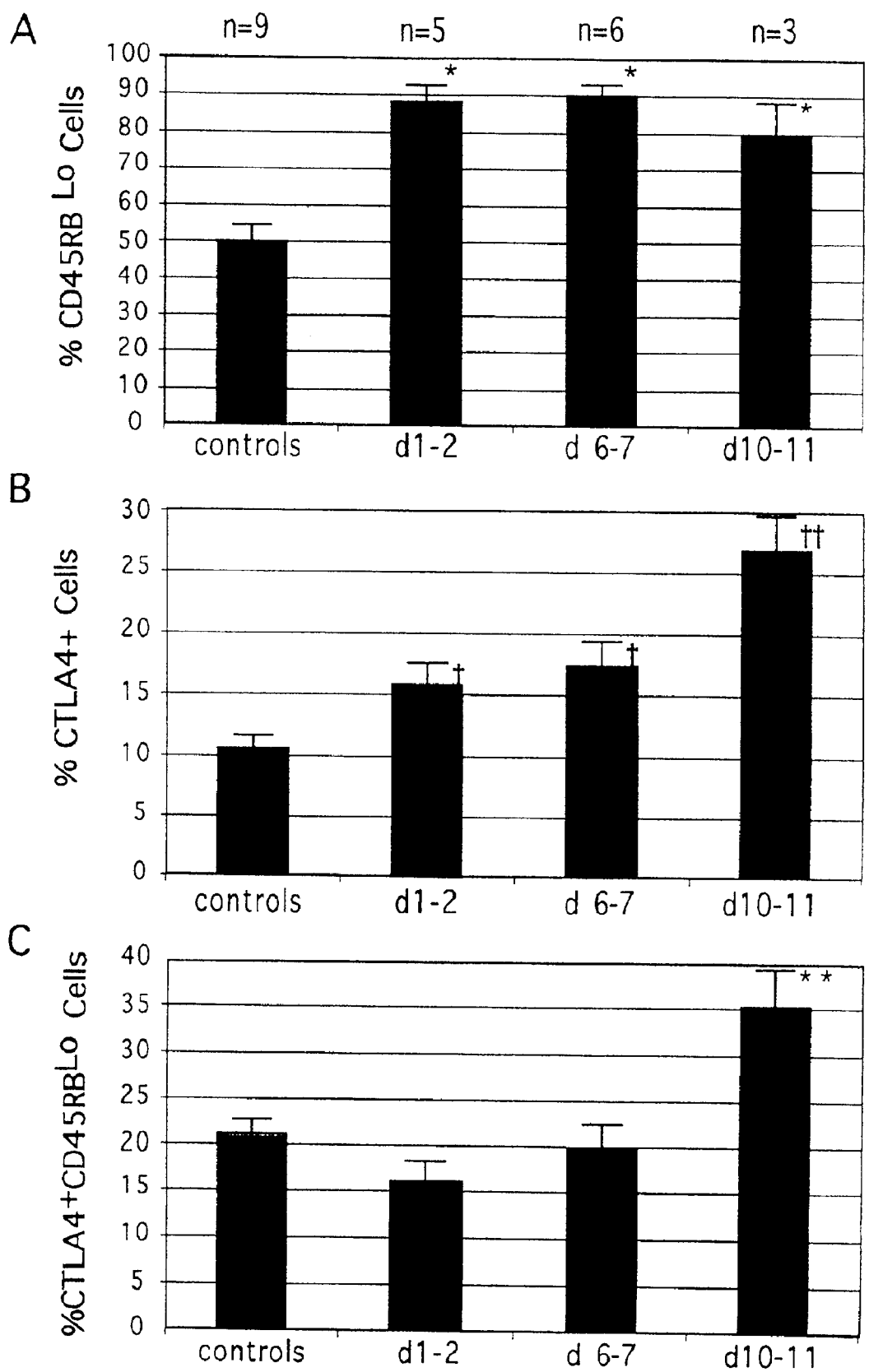

FIG. 3 comprises bar graphs showing data related to the time-course of the shift in CD45 isoforms and CTLA-4 induction after anti-CD45RB treatment. Splenocytes were isolated from untreated and treated animals at various time-points after initiation of treatment with anti-CD45RB. CD4+ splenocytes were examined by 3-color immunofluorescence as described above. Data are expressed as the percent of CD4 cells expressing $CD45RB^{Lo}$ (Panel A); Percent of CD4 cells expressing CTLA4 (Panel B); and CTLA4 expression on CD4+ $CD45RB^{Lo}$ cells (Panel C). Data are depicted as the mean (+S.D.) for 3–9 animals in each group as indicated. $*\leq 0.001$ vs. control; $\dagger \leq 0.015$ vs. control; $\dagger\dagger \leq 0.0001$ vs. Control and $p \leq 0.025$ vs. other groups; $**p<0.03$ vs. all other groups.

Figure 4:
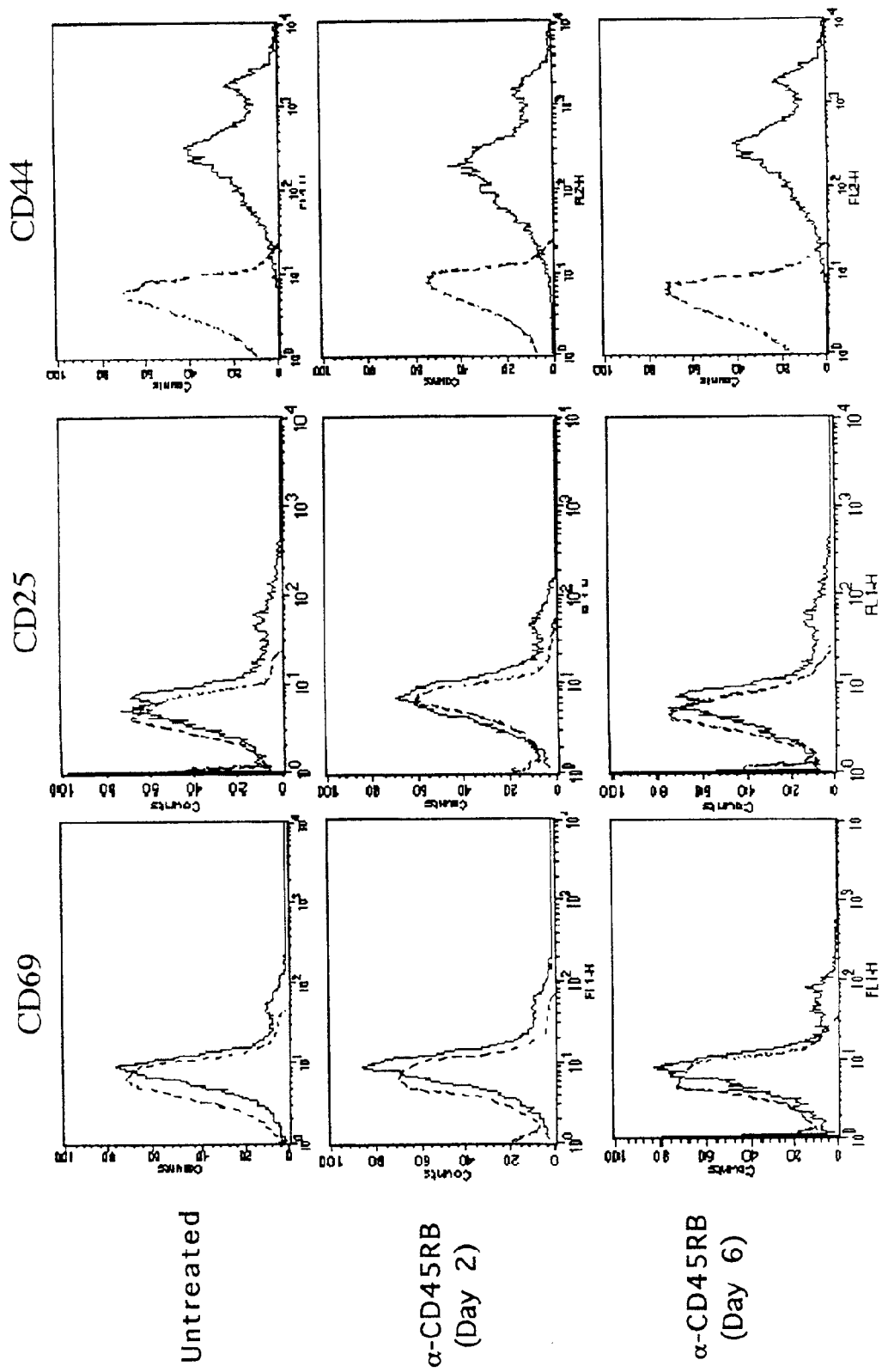

FIG. 4 are histograms providing evidence that anti-CD45RB treatment does not induce expression of other activation markers. Shown are single color histograms of CD69, CD25 and CD44 expression on CD4 cells from untreated control animals and animals on day 2 and day 6 after initiation of treatment with 3 doses of anti-CD45RB. The dotted lines in each histogram represent immunofluorescence of isotype controls. The x and y axes represent log fluorescence and cell number, respectively. Similar results were obtained in at least 3 experiments in each group.

Figure 5:
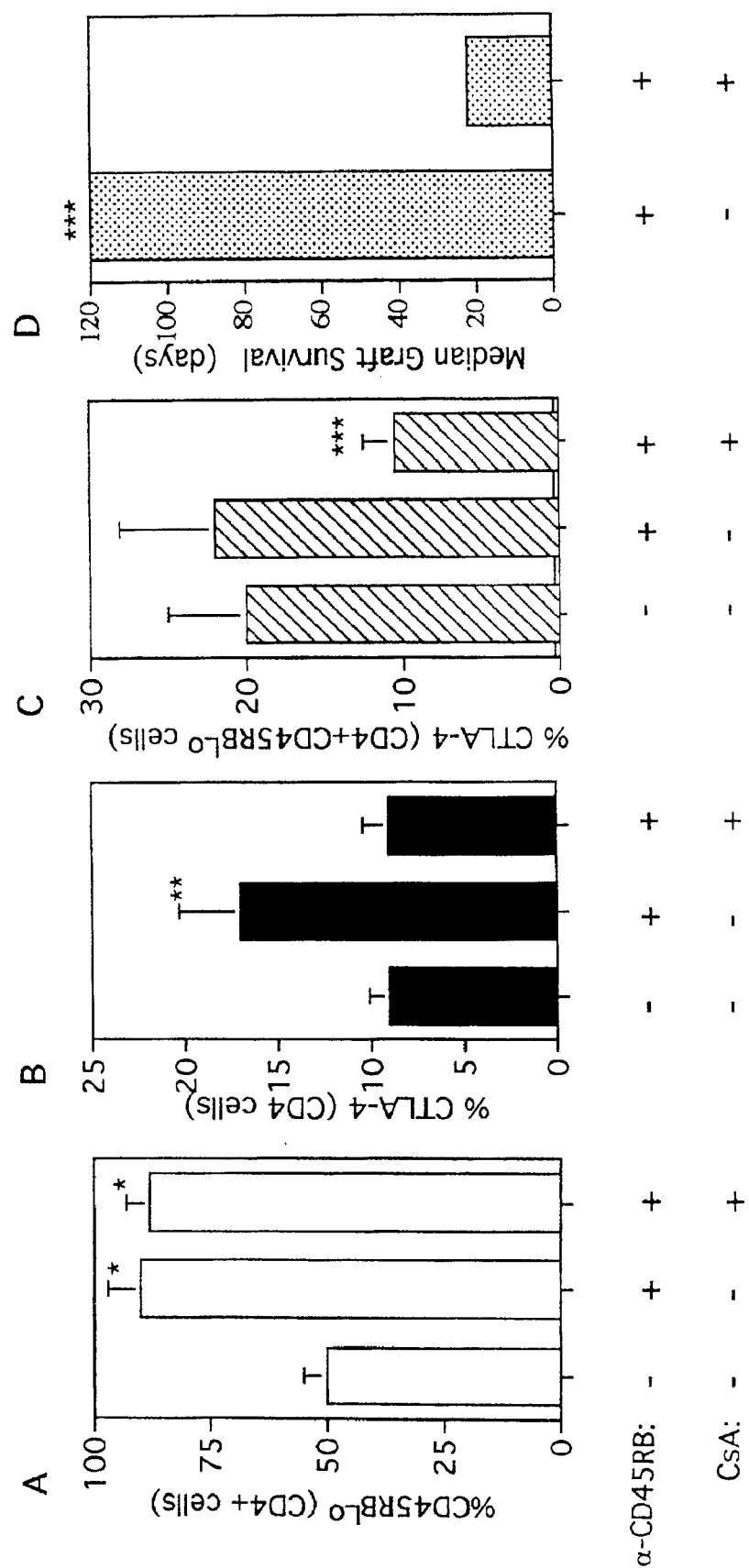

FIG. 5 employs bar graphs showing that Cyclosporin A (CsA) blocks the anti-CD45RB -mediated increase in CTLA-4 expression on CD4 cells and inhibits prolongation of allograft survival. Panels A–C: Mice were untreated, received anti-CD45RB alone, or received anti-CD45RB plus CsA. On day 6, splenocytes were evaluated by 3 color-immunofluorescence as described above. CD4 cells were evaluated for: $CD45RB^{Lo}$ expression (Panel A); CTLA-4 expression (Panel B); Or CTLA-4 expression on $CD45RB^{Lo}$ cells (Panel C). Results are expressed as mean percent of cells positive (+S.D.) for 4 animals in each treatment group. $*p \leq 0.0001$ vs. Control; $p \leq 0.004$ vs. other groups; $*p \leq 0.02$ vs. other groups. Panel D: Chemically diabetic C57BL/6 recipients received islet allografts from BALB/c donors and received either anti-CD45RB alone, or anti-CD45RB plus CsA (n=7). Data are represented as median graft survival. ***p=0.014 CsA treatment vs. no CsA.

Figure 6:
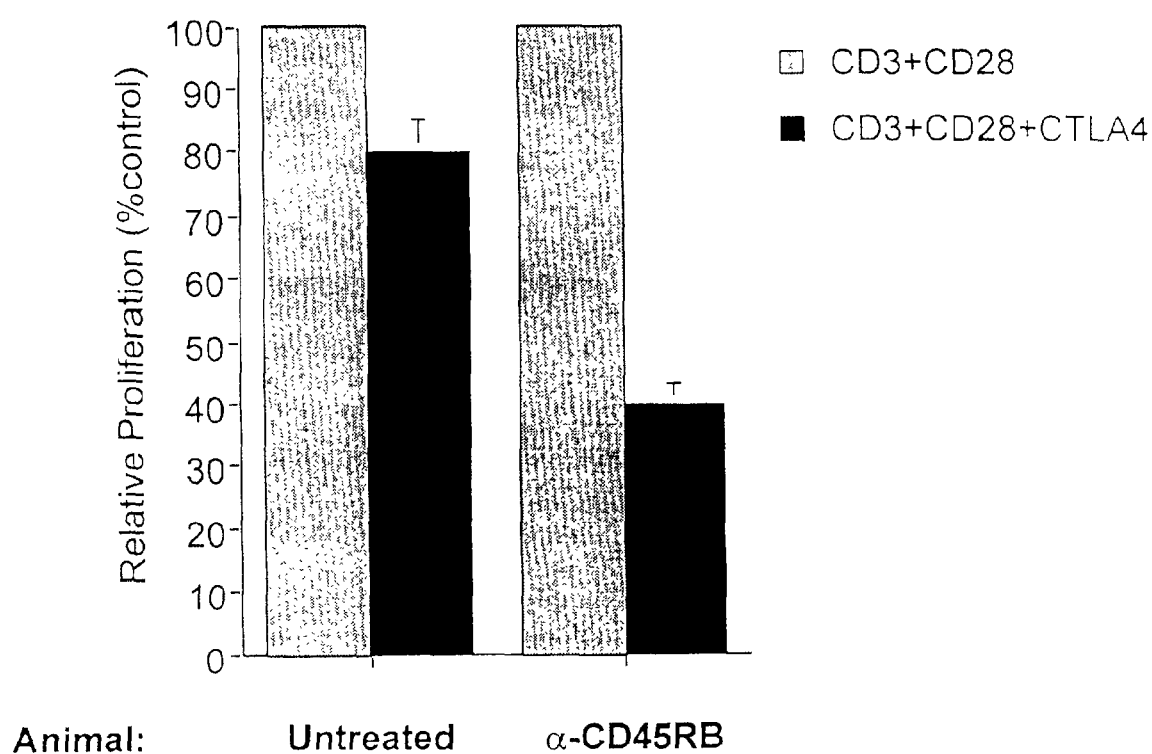

FIG. 6 employs a bar graph to show that anti-CD45RB treatment (in vivo) to induce CTLA-4 expression is associated with increased sensitivity to anti-CTLA-4 mediated inhibition of cellular proliferation in vitro. CD4 cells were isolated from the spleens of untreated and anti-CD45RB treated mice on day 7 and placed into 96-well flat bottom plates along with latex beads coated with either anti-CD3+ anti-CD28 (Control) OR anti-CD3+ anti-CD28 plus anti-CTLA-4 (experimental). After 2 days, cells were pulsed with H3-thymidine. Cell proliferation was determined using DNA synthesis as measured by H3-thymidine incorporation. Data are displayed as relative proliferation of CD4 cells after CD3/CD28/CTLA-4 crosslinking in comparison to that of control cells (stimulated in the absence of CTLA-4 crosslinking). Data are the mean plus standard error (SEM) of three experiments.

Figure 7:

FIG. 7 utilizes a bar graph to show that in vitro upregulation of CTLA-4 expression by anti-CD45RB and by T cell activation have distinct kinetics and are at least in part additive at each time point. These data support the notion that these stimuli upregulate T cell activation independently. Murine splenocytes were added at $5\times10^6$ cells per well (48 well plate). Cells were untreated (controls), were treated with soluble anti-CD45RB (MB23G2), were plated in wells that were pre-coated with anti-CD3 and anti-CD28 to induce T cell activation, or were placed in pre-coated wells and were treated with anti-CD45RB. At 4 hours and 24 hours after plating, cells were removed and CD4+splenocytes were examined by 3-color immunofluorescence staining for CD4, CD45RB and intracellular CTLA-4 (permeabilized cells). CTLA-4 expression on CD4+ lymphocytes was calculated based on the fluorescence pattern using isotype/species matched negative control antibodies, and are displayed as relative CTLA-4 expression in comparison to CTLA-4 expression on control cells at each time point (100%). The data are the mean plus standard error (SEM) of 3 experiments.

Figure 8:
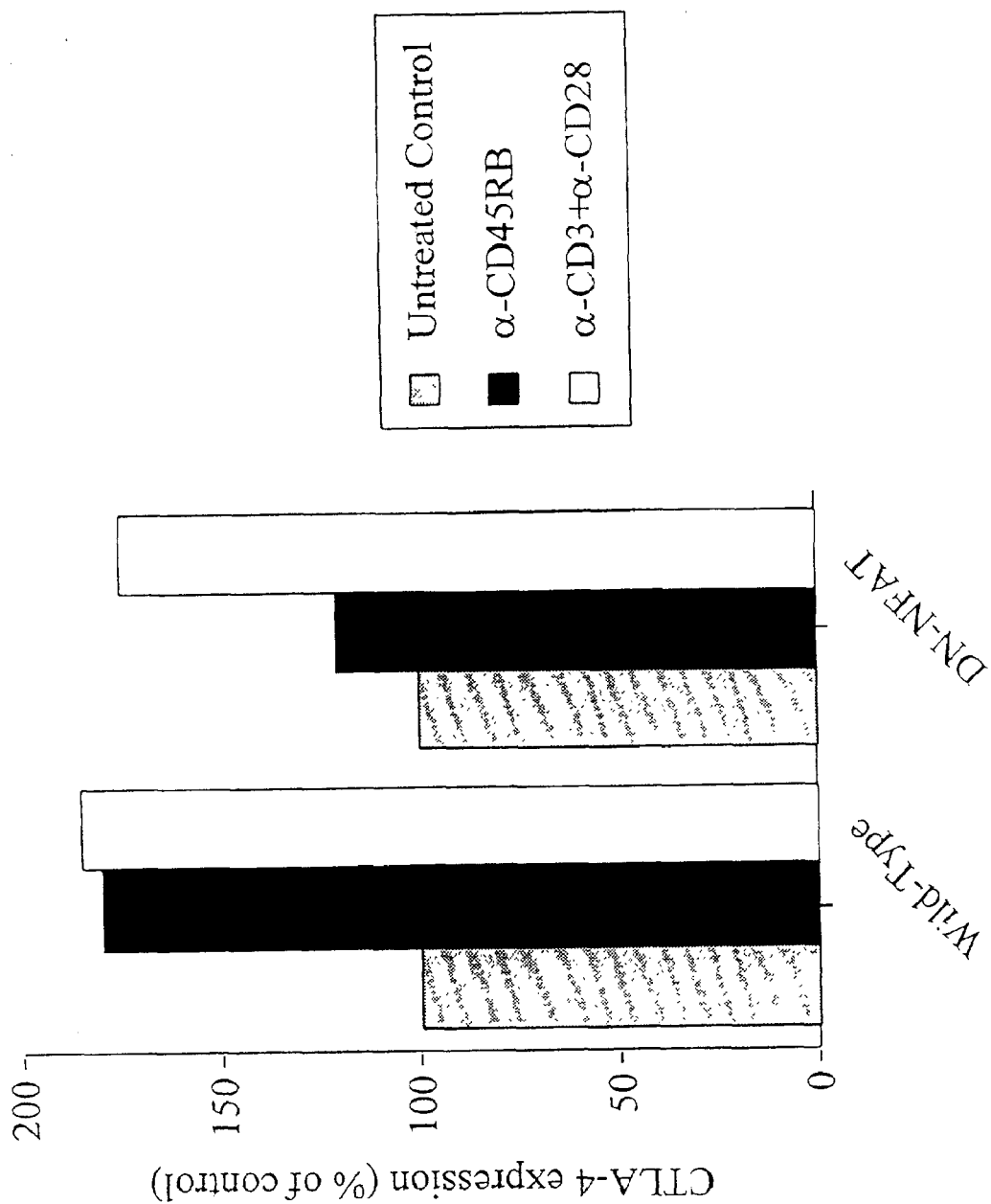

FIG. 8 employs a bar graph to show that in vitro upregulation of CTLA-4 expression by anti-CD45RB but not that induced by T cell activation is dependent on the NFAT transcription factor. Murine splenocytes were added at $5\times10^6$ cells per well (48-well plate) from either wild-type B10.BR mice or B10.BR mice expressing a dominant-negative transgene for the NFAT transcription factor (Chow, et al., *Mol Cell Biol* 19:2300, 1999). Cells were untreated (controls) or were treated with soluble anti-CD45RB (MB23G2), were plated in wells that were pre-coated with anti-CD3 and anti-CD28 to induce T cell activation. At 4 hours and 24 hours after plating, cells were removed and CD4+ splenocytes were examined by 3-color immunofluorescence staining for CD4, CD45RB and intracellular CTLA-4 (permeabilized cells) and CTLA-4 expression shown relative to control mice (100%) form each mouse strain. The data are representative of 3 experiments.

DETAILED DESCRIPTION OF THE INVENTION

Previous evidence suggested that CTLA-4 expression could only be augmented by full-scale T cell activation and entry of the T cell into the cell cycle. The current invention is based upon the finding that CTLA-4 expression can actually be differentiated from other aspects of T cell activation and can be specifically increased to enhance immunosuppression and immunologic tolerance.

The invention provides screens that identify agents useful in promoting immunosuppression or tolerance by directly or indirectly measuring or observing enhancement of CTLA-4 levels or activity in vivo in animals and in vitro in mammalian cells in culture. Screening methods of the invention employ any animals such as, but not limited to, mice, rats, pigs, dogs, cats, non-human primates and human subjects. Many preferred embodiments employ mice and non-human primates in initial screens, and human subjects in later screens that aim to identify especially efficacious agents. Mammalian cell cultures include, but are not limited to, primary T-lymphocytes derived from the spleen, lymph node, thymus, or peripheral blood, tissue samples, or T cell lines or clones derived from of the species listed above, and the like, which express CTLA-4. However, as will be discussed more fully below, some screens employ animal phenotypes that are CTLA-4 deficient and mammalian cell cultures that do not express CTLA-4.

In a typical method for directly screening for an agent useful in promoting immunosuppression or immunologic tolerance in a mammal, a test agent is administered to an experimental animal, a biological sample is taken from the animal and from a control animal of the same species, and the cell surface, cytoplasmic, or cell surface and cytoplasmic levels of CTLA-4 in both samples are measured. The levels in the control and experimental animals are compared and test agents of use in promoting immunosuppression or immunologic tolerance are identified by observation of increased levels of CTLA-4 in the test animal sample over the CTLA-4 levels in the control animal sample. As mentioned above, any type of biological sample of material that contains or expresses CTLA-4 in nature may be employed, such as, but not limited to, cells, blood, plasma, serum, lymph nodes, splenocytes, tissues, and the like may be employed. Samples comprising T-lymphocytes are preferred in many embodiments.

In a second typical method for directly screening for agent useful in promoting immunosuppression or immunologic tolerance in a mammal, a test agent is administered to a biological sample (e.g., cells, cell lines, or tissues) in vitro and examined for CTLA-4 expression compared to control samples not treated with the agent. Samples comprising T-lymphocytes are preferred in many embodiments.

Any type of assay or determination used to determine CTLA-4 levels in the samples may be employed, such as, but not limited to, immunoassays, including direct competitive, sandwich, direct and indirect cellular, and crisscross enzyme-linked immunosorbent assays (ELISAS), radioimmunoassays (RIAs), immunoprecipitation, immunohistochemistry, immunofluorescence, immunoblotting, and the like may be employed using polyclonal, monoclonal, polyclonal, and fusion phage antibodies. Simple immunofluorescence using monoclonal and/or fusion phage antibodies are especially preferred in many embodiments.

A method wherein the biological sample comprises cells that are fixed, permeabilized, and incubated with an anti-CTLA-4 tagged antibody prior to comparison is illustrated in the Examples that follow. Direct protein measurement may also be employed, including, but not limited to, colorometric analysis, electrophoretic separations, gel filtration, ion-exchange chromatography, hi-performance chromatography (HPLC or other), hydrophobic interactive chromatography, size-exclusion chromatography, size-exclusion-high-performance chromatography, reversed phase chromatography, Western blotting, and the like may be employed, including indirect methods that measure mRNA levels. It is an advantage of the invention that CTLA-4 has been studied in some detail, so that many antibodies to CTLA-4, including commercial preparations, are available, as are published descriptions of how to develop others. Moreover, the sequence of CTLA-4 is known so that assessment of mRNA levels by PCR, ribonuclease protection assays, or Northern analysis, are feasible. Alternatively, since its promoter region has been sequenced, the CTLA-4 promoter could be fused to a reporter gene to form a reporter construct that could be expressed in cell lines (by transfection or viral transduction) or expressed as a transgene in transgenic animals. Finally, the CTLA-4 gene could be expressed heterologously (in cell types that do not normally express CTLA-4) under control of its endogenous or a viral promoter, and used to examine the effects of a test agent on CTLA-4 levels or function in in vitro or in vivo models.

A number of in vivo, in vitro and mixed in vivo/in vitro screens employ anti-CTLA-4 antibodies and/or CTLA-4-deficient animals. For example, one method screens for agents by (a) administering a test agent to an animal, and (b) administering an anti-CTLA-4 antibody and the test agent to another animal of the same species; maintaining the animals under the same conditions for a time sufficient for the animals in (b) to develop at least one clinically observable sign of an immune response that is not seen in the animals in (a) such as rejection of a transplanted organ or cells, abnormal blood values (e.g., glucose, creatinine, lymphocyte counts), abnormal urine values (e.g., protein or glucose), abnormal histopathology, lymphadenopathy, abnormal gait, failure to thrive, weight loss, or death; and identifying a useful test agent by observation that the anti-CTLA-4 antibody interfered with the ability of the test agent to block an immune response in the animal to which it was administered.

A CTLA-4-deficient animal may be employed instead of anti-CTLA-4 antibodies. A test agent is (a) administered to a normal animal and (b) administered to a CTLA-4-deficient animal of the same species; the animals are maintained under the same conditions for a time sufficient for the animals in (b) to develop at least one clinically observable sign of an immune response that is not seen in the animals in (a); and useful agents are identified by observation that the CTLA-4 deficiency interfered with the ability of the test agent to block an immune response in the animal to which it was administered. In either case, biological samples can be obtained after the animals have been maintained for a time sufficient to observe an immune response and tested in functional assays such as cytokine production, cell proliferation, cell death, and the like, to assess whether or not the agent interferes with the assay.

In an alternate embodiment: a) a test agent is added to mammalian cells in culture that express CTLA-4; b) the test agent plus anti-CTLA-4 antibody are added to similar mammalian cells that express CTLA-4 in culture, or the test agent is added to similar mammalian cells that lack CTLA-4 expression; c) the cultures are tested in functional assays including, but not limited to cytokine production, cell proliferation, cell death (cytotoxocity or apoptosis), or any combination thereof; and d) useful agents are identified by observation that anti-CTLA-4 antibody or CTLA-4 deficiency interfered with the activity of the agent in the functional assay. Such cells, initially treated with the agent in vitro could also be adoptively transferred into host animals and examined for similar functional activities or clinical outcomes in vivo. As before, agents are selected based upon the ability of anti-CTLA-4 (administered in vivo or in vitro) or CTLA-4 deficiency to interfere with their immunosuppressive or tolerogenic activity as an indication that the agent acts through augmentation of CTLA-4.

An advantage of the invention is that immunology in general and autoimmunity and T-cell mediated immunity have been studied for years, and much is known about properties of the complex system as a whole. A variety of pharmaceutical compositions have been suggested as immunomodulators that prevent or reverse organ transplant rejection in primates. These include anti-CD3-immunotoxin combined with Deoxyspergualin (DSG) (Thomas, J. M., et al., *Transplantation* 68:480–484), anti-CD40L (Kirk, A., et al., *Proc Natl Acad Sci USA*. 94: 8789–94), protocols designed to induce mixed chimerism using bone marrow infusions with a conditioning regimen (Spitzer, T. R., et al., *Transplantation* 72:351–354) and anti-CD45RB antibodies, each of which inhibits T-cell mediated immune responses (e.g., U.S. Pat. Nos. 6,024,957, 6,099,838, and 6,106,834 to Lazarovits and Poppema). The applicants' novel finding that CTLA-4 expression can be specifically upregulated provides a unique opportunity to harness this potent downregulatory pathway to promote immunosuppression and transplant tolerance for the prevention of rejection and treatment and prevention of autoimmune diseases. None of the aforementioned agents in preclinical trials and no other published experimental agents used in animal models of transplantation or autoimmune disease, have ever been shown to work by augmenting CTLA-4. Given the fundamental importance of CTLA-4 in dampening the immune response and in the generation and maintenance of peripheral tolerance, it is highly likely that the development of specific agents that augment this inhibitory pathway will provide an important new therapeutic tool for the treatment of immune-mediated diseases. It is envisioned that agents targeting CTLA-4, either used alone or in combination with other immunotherapeutic agents, will help us achieve the elusive goal of immunological tolerance. This will have a great impact on the prevention and treatment of autoimmune diseases such as diabetes, rheumatoid arthritis, psoriasis, and systemic lupus erythematosis. Moreover, such agents are likely to help make cellular transplants, such as islets, hepatocytes, stem cells, and transplants from animals (xenografts) feasible, easing the organ shortage and making transplantation practical for many more patients.

EXAMPLES

The following examples are presented to further illustrate and explain the present invention and should not be taken as limiting in any regard. The examples provide evidence that treatment with a particular anti-CD45RB monoclonal antibody (termed clone MB23G2) alters CD45 isoform expression on T cells which is associated with rapid upregulation of CTLA-4 expression. These effects appear specific, occurring without upregulation of other activation markers. Administration of a blocking mAb against CTLA-4 at the time of transplantation prevents anti-CD45RB therapy from prolonging islet allograft survival. Moreover, concomitant treatment with Cyclosporin A blocks anti-CD45RB-induced CTLA-4 expression and promotes acute rejection. These data suggest that anti-CD45RB acts through novel mechanisms that include CTLA-4 upregulation and demonstrate a link between CD45 and CTLA-4 that depends on calcineurin-mediated signaling. Moreover, they demonstrate for the first time that CTLA-4 expression may be specifically targeted to enhance allograft acceptance.

A model has been established whereby splenocytes, purified T cells, or isolated CD4 T can be treated with anti- CD45RB in vitro. A two-fold increase in CTLA-4 levels (cytoplasmic) is observed within 4 hours. In contrast, T cell activation (with antibodies against the T cell receptor (CD3) and CD28 costimulatory molecule) show completely distinct kinetics, having no effect at 4 hours and requiring 24 hours before a two-fold increase in CTLA-4 is observed. CTLA-4 upregulation by T cell activation and by anti-CD45RB are additive at each time-point indicating that they utilize at least partially distinct pathways. These data demonstrate the feasibility of in vitro screening assays and provide additional evidence that CTLA-4 expression can be targeted specifically and independently from T cell activation. This latter point is further supported by data indicating that the increase in CTLA-4 expression mediated by anti-CD45RB but not that mediated by T cell activation is dependent an intact NFAT transcription factor. This transcription factor lies immediately downstream from calcineurin and as such, these findings provide additional targets for pharmacological intervention aiming to upregulate CTLA-4. In this regard, it should be noted that not all anti-CD45 (or anti-CD45RB) mAbs upregulate CTLA-4 expression. Moreover, we expect that other agents will be discovered using the screening tests described herein, that will promote immunosuppression of tolerance thorough modulation of CTLA-4 levels or activity.

Finally, anti-CD45RB-induced augmentation of CTLA-4 results in increased sensitivity to inhibition through CTLA-4-mediated signaling in vitro as well as in vivo. Specifically, co-cross-linking anti-CD3, anti-CD28, and anti-CTLA-4 on latex beads has been shown to provide the necessary stimulus required for negative signaling through CTLA-4. Cells treated with anti-CD45RB to upregulate CTLA-4 expression show greater anti-CTLA-4 mediated inhibition of cellular proliferation than unmodified cells—demonstrating greater sensitivity to CTLA-4 mediated inhibitory signaling. Taken together, our data demonstrate that CTLA-4 augmentation is functionally relevant both in vitro in a proliferative assay and in vivo, where it promotes long-term islet allograft survival.

Materials and Methods

Animals: 7–10 week old male C57BL/6 (H-2b) recipients and BALB/c (H-2d) donor mice (Charles River Boston Mass.) were housed individually after transplantation with free access to food and water.

Antibodies: For in vivo use, the anti-CD45RB mAb MB23G2 (ATCC, Rockville, Md.) and the anti-CTLA-4 mAb 4F10 were purified on protein G columns according to the manufacturer's instructions (Pharmacia, Piscataway, N.J.). For in vitro use: Anti-CD8 (TIB210, ATCC), B220 (TIB164, ATCC), anti-MHC Class II (212.A1), anti-FcR (24G2), were employed. Purified anti-CD3 (2C-11) and anti-CD28, and fluorochrome-conjugated mAbs against CD3, CD4, CD8, CD25, CD44, CD45, CD45RB, CD69, and CTLA-4 as well as fluorochrome-conjugated Hamster-Ig and Rat-Ig control antibodies were from Pharmingen.

Islet Isolation and Transplantation: Diabetes was induced in C57BL/6 mice with streptozotocin (200 mg/kg, ip) and confirmed by persistent hyperglycemia (blood glucose, >400 mg/dl). After in situ digestion with collagenase P (Sigma, St. Louis, Mo.), islets were separated by density gradient centrifugation and 400 hand-picked islets were transplanted under the left kidney capsule, as described[26]. Glycemia of <200 mg/dl by day 3 after transplantation and >250 mg/dl (after initial engraftment) defined primary graft function and graft loss, respectively. All in vivo studies were performed in compliance with NIH and Yale Animal Care and Use Committee guidelines.

Treatment Protocols: Recipient mice received 100 ug iv anti-CD45RB (MB23G2) on days –1, 0, and 5, as previously described[26]. Anti-CTLA-4 was administered as 200 ug ip on days –1, 0, and 1[8]. CsA was administered at 20 mg/kg/d ip[44] on day –3 through day 7. Control allograft recipients were untreated.

Immunofluorescence: mAbs were used at saturating concentrations to analyze surface expression by two and three-color direct immunofluorescence. CD45RB expression was analyzed by staining with FITC-conjugated anti-CD45RB mAb (clone 16A) which does not cross-react with the epitope bound by MB23G2. Cell surface expression of CTLA-4 was obtained by standard immunofluorescence on non-permeabilized cells. Intracellular CTLA-4 expression was examined by fixing cells in 2% paraformaldehyde followed by permeabilization with 0.5% saponin followed by incubation with anti-CTLA-4-phycoerythrin or Hamster-Ig-phycoerythrin control Ab, as described[9]. In the case of multi-color analysis, cells were stained with other markers before incubation with saponin. Cell phenotype was analyzed by using a BD FACStar (5,000 cells per sample), as described[26]. Negative controls used rat or hamster IgG fluorochrome conjugates.

Activation-induced CTLA-4 expression: CD4 cells were purified from splenocytes from treated and untreated animals by negative selection using a cocktail of mAbs against FcR, Class II, B220, and CD8, followed by incubation with anti-rat Ig and anti-murine IgG and IgM coated immunomagnetic beads (Biomag; PerSeptive Diagnostics, Cambridge Mass.). CD4 cells (50,000 cells/well) were placed in 96-well flat bottom plates that had been previously coated with anti-CD3 (10 ug/ml) and anti-CD28 (10 ug/ml), as described[9,28]. Cells were incubated for 4 hours at 37° C. in the presence of phycoerythrin conjugated anti-CTLA-4 or Hamster IgG control, washed, stained with anti-CD45RB (16A), and then analyzed via flow cytometry. To differentiate between activation-induced accumulation of CTLA-4 on the cell surface versus the intracellular compartment (due to endocytosis), CD4 cells in parallel wells were cultured for 4 hours (without anti-CTLA-4) and were then stained for surface expression with anti-CTLA-4 or Hamster-Ig control (at 4° C.), as described[9,28].

Anti-CTLA-4 mediated inhibition assays: Otherwise naive mice received no treatment or received 3 doses of anti-CD45RB (MB23G2). On day 7, splenic CD4 cells were isolated by negative selection using immunomagnetic beads, as described above. CD4 cells (50,000 cells/well) were placed in 96-well flat bottom plates at a 1:1 ration with latex beads (Interfacial Dynamics Corp) that had been pre-coated with anti-CD3 (0.25 ug/ml), anti-CD28 (0.5 ug/ml) and either hamster IgG (control) or anti-CTLA-4 (both at 5 ug/ml), as described by Krummel, et al. (*J Exp Med.* 182:459–465, 1995). After 48 hours in culture, plates were pulsed with 1 uCi of H3-Thymidine for 16 hours and cells were harvested. The relative proliferation was determined by comparing of H3-Thymidine (C.P.M.) of cells stimulated with control beads (anti-CD3 and anti-CD28 coated beads= 100%) versus proliferation of cells stimulated with beads coated with anti-CD3, anti-CD28, and anti-CTLA-4.

CTLA-4 Upregulation in vitro: $1-5 \times 10^6$ splenocytes, negatively selected T cells, or CD4 cells, were placed in 1 ml of RPMI tissue culture media alone, or in the presence of anti-CD45RB (3 ug/ml). At various times, cells were removed and analyzed by 3-color immunofluorescence after staining with anti-CD4 and anti-CD45RB followed by permeabilization and staining with anti-CTLA-4 (to detect both surface and cytoplasmic CTLA-4). In addition, cells were stained with antibodies against various markers for adhesion and activation, including CD11 b, CD29, CD44, CD69 and CD25, which were all unchanged.

To examine the effects of T cell activation, cells isolated as above were incubated in wells that were coated with anti-CD3 plus anti-CD28 (10 ug/ml each), as described above. In additional wells, cells were stimulated with anti-CD3 plus anti-CD28 in addition to anti-CD4RB.

Finally, similar experiments were also carried out whereby the response of cells from wild-type mice were compared with those from mice heterozygous for a transgene encoding for a dominant negative version of the NFAT transcription factor (exhibiting only 20–25% of wild-type NFAT activity).

Statistical Analysis: Graft Survival was compared using the Mann-Whitney test. Other analyses used the Student t-test.

Results

Anti-CD45RB-mediated engraftment requires CTLA-4 Signaling. The role of CTLA-4 in long-term engraftment resulting from anti-CD45-mediated interference with signal one, is unknown. To address this question, we determined whether or not CTLA-4 blockade would prevent long-term survival of islet allografts by anti-CD45RB. Untreated control animals rapidly reject their allografts, becoming hyperglycemic in 11–12 days (Table 1, below). Treatment of recipients with 3 doses of anti-CD45RB (MB23G2) as sole therapy, results in long-term engraftment in approximately 50% of the recipients in this high-responder strain combination. However, when recipients received a blocking mAb against CTLA-4 at the time of engraftment, anti-CD45RB was no longer able to promote long-term engraftment and the recipients rejected promptly (MST 22 days). This was not due to a generalized augmentation of the rejection response by CTLA-4 blockade, because animals treated with anti-CTLA-4 alone did not reject their grafts more quickly than untreated controls.

The rapidity with which anti-CD45RB treated animals rejected grafts when the CTLA-4 pathway was blocked, raised the question as to whether CTLA-4 signals were directly involved in anti-CD45RB-mediated engraftment. For example, anti-CTLA-4 might prevent induction of a requisite shift in CD45 isoforms by anti-CD45RB.

Figure 1:
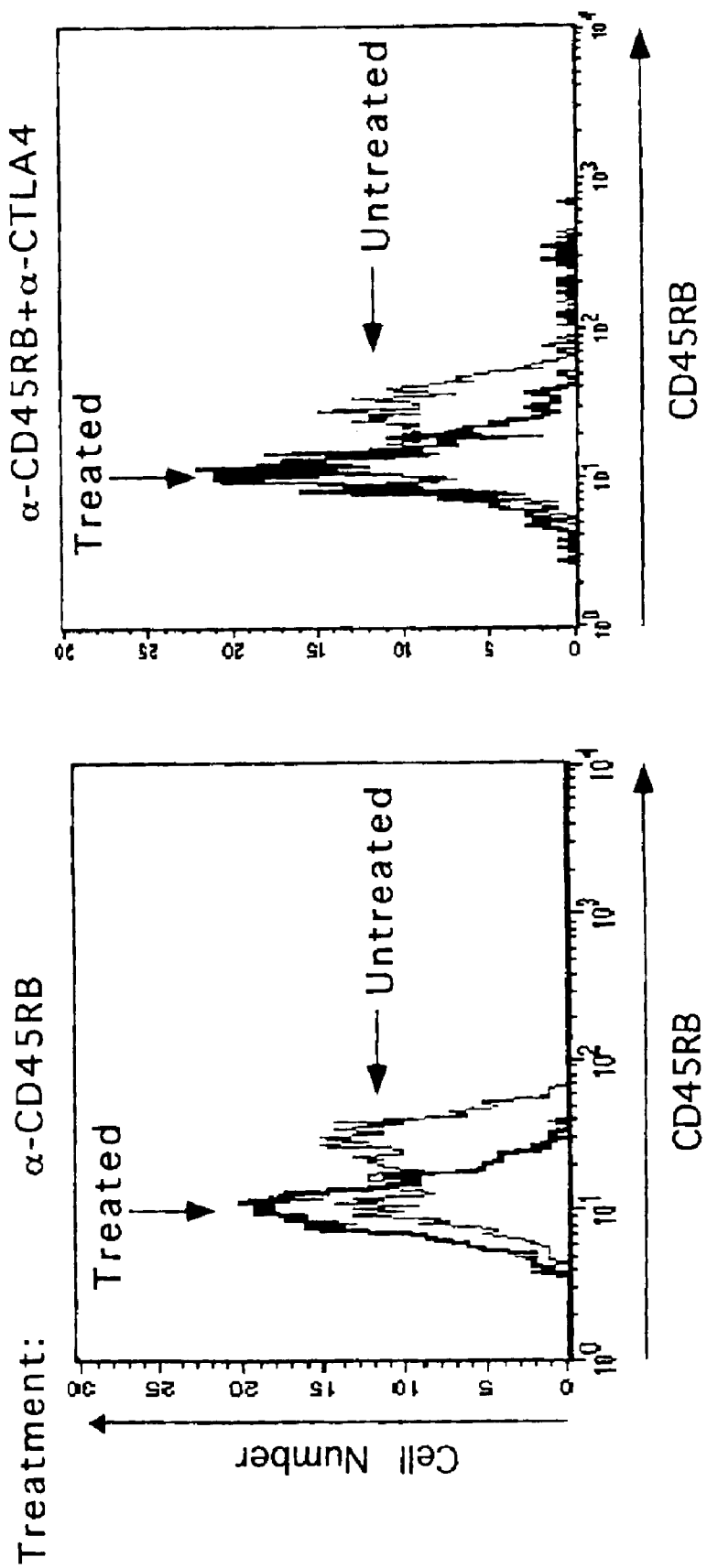
FIG. 1 depicts fluorescence plots showing that anti-CTLA-4 does not alter the anti-CD45RB-mediated shift in CD45 isoforms. Representative CD45RB expression on CD4+ cells from untreated vs. anti-CD45RB treated animals (left panel); and untreated vs. anti-CD45RB plus anti-CTLA-4 treated animals (right panel). Splenocytes were isolated from mice on day 6 after treatment with 3 doses of anti-CD45RB (MB23G2), or 3 doses each of anti-CD45RB and anti-CTLA-4. After gating on CD4+ cells, CD45RB expression was analyzed. The x and y axes represent log fluorescence and cell number, respectively. Fluorescence of isotype controls was always within the first decade and did not differ between treatment groups. Similar results were obtained in 4 independent experiments.

Anti-CTLA-4 does not influence regulation of CD45 isoforms. To address this latter point, we compared CD45RB expression on CD4 cells from animals treated either with anti-CD45RB alone or the combination of anti-CD45RB plus anti-CTLA-4. In both cases, an equivalent loss of CD45RB high isoforms was apparent (FIG. 1). There was little or no change in overall CD45 expression, indicating a concomitant upregulation of lower Mr isoforms (ref[26]). Furthermore, there was no change in the total number of T cells in the spleen, indicating that simple depletion of CD45RB$^{Hi}$ cells (~50% of the CD4 population) had not occurred. Thus, anti-CTLA-4 does not inhibit the shift in isoforms induced by anti-CD45RB.

Figure 2A:
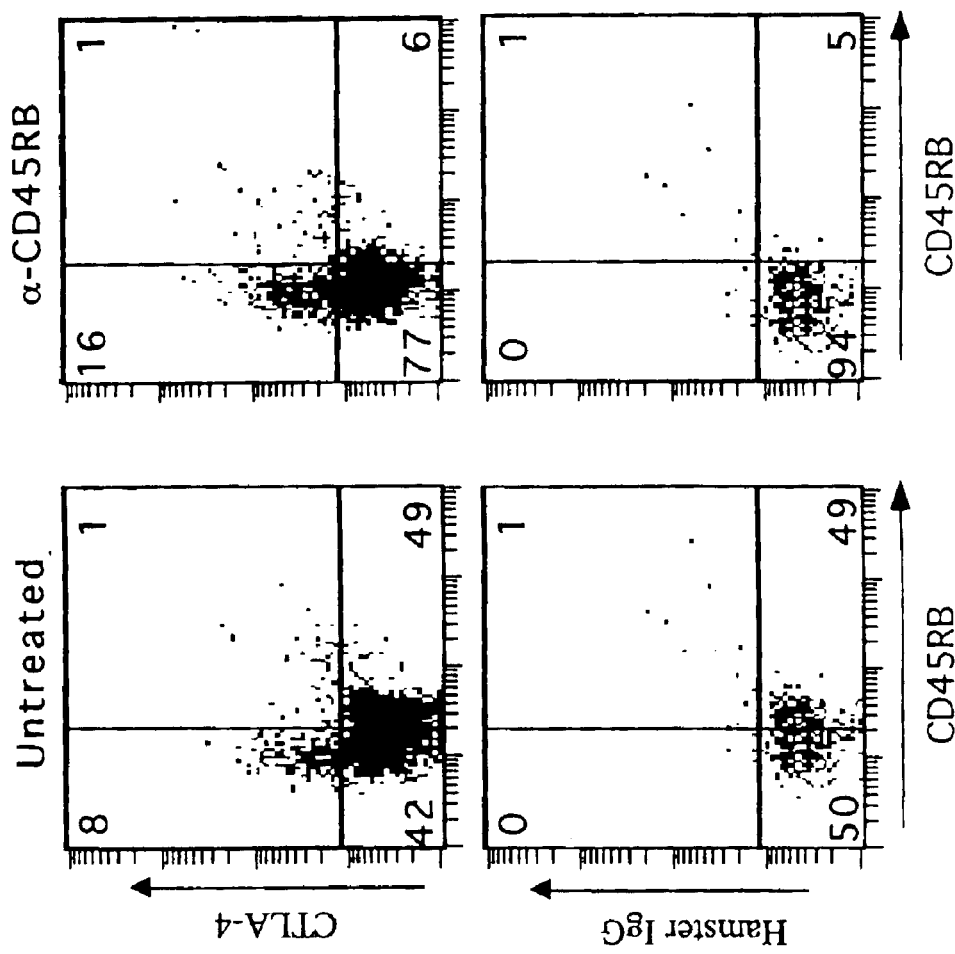
FIG. 2 depicts CTLA-4 expression by immunofluorescence and demonstrates that CTLA-4 is upregulated by anti-CD45RB treatment.

Anti-CD45RB treatment upregulates CTLA-4 expression. While virtually undetectable in freshly isolated CD45RB$^{Hi}$ CD4 cells, CTLA-4 is constitutively expressed by a proportion of "antigen experienced" CD45RB$^{Lo}$ cells that appear primed towards down-regulation through this pathway[28]. Given that anti-CD45RB treatment induces a shift from high to low (CD45RB$^{Lo}$) Mr CD45 isoforms and prolongation of allograft survival by anti-CD45RB is highly dependent on CTLA-4 signaling, it is possible that anti-CD45RB acts by upregulating CTLA-4 expression. To answer this question, we compared CTLA-4 expression on CD4+ cells from mice receiving anti-CD45RB treatment with CD4+ cells from untreated control mice (FIG. 2a). As CTLA-4 expression is primarily intracellular, CTLA-4 expression was examined on permeabilized cells. In untreated control animals, CTLA-4 was constitutively expressed by a population of CD45RB$^{Lo}$ cells. As shown, ~20% of the CD45RB$^{Lo}$ population constitutively expresses CTLA-4. Because only ~50% of the resting population of CD4 cells is CD45RB$^{Lo}$, just 10% of the overall CD4 population expresses CTLA-4. On day 6 after initiation of treatment with anti-CD45RB, ~95% of the CD4 cells are CD45RB$^{Lo}$, and constitutive CTLA-4 expression essentially doubles (FIG. 2a).

Figure 2B:
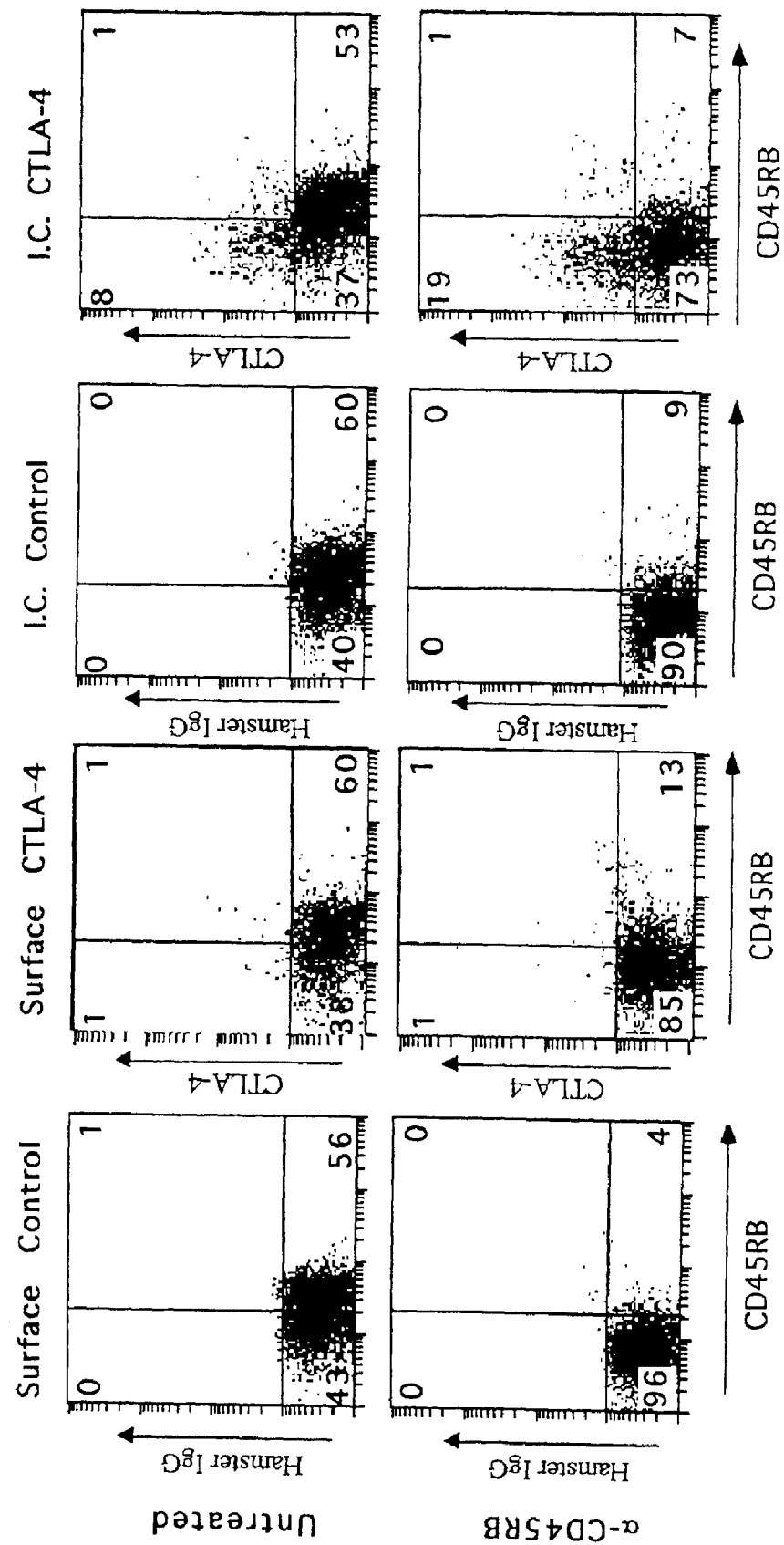

While CTLA-4 expression remains primarily intracellular, T cell activation results in rapid cycling of pre-formed CTLA-4 between endosomal compartments and the cell surface[9,10,29]. To examine regulation of this axis after induction of CTLA-4 expression by anti-CD45RB, CD4 cells from treated (day 6, after anti-CD45RB) and untreated animals were activated in wells coated with anti-CD3 and anti-CD28. After 4 hours, CD4 cells from both treated and untreated animals exhibited only minimal surface expression of CTLA-4 (FIG. 2b). However, addition of fluorochrome-conjugated anti-CTLA-4 to the cells during short-term (4 h) activation resulted in internalization of mAb as CTLA-4 cycles to the surface and back (as described[9,28]). In this case, anti-CD45RB-treated animals exhibit CTLA-4 expression on twice as many CD4 cells as untreated animals (FIG. 2b). This agrees closely with the results obtained by direct (intracellular) staining of permeabilized cells (FIG. 2a). Thus, CTLA-4 induced by anti-CD45RB has rapid access to the cell surface and undergoes normal regulation of surface expression and endocytosis.

Examination of the time-course of changes in CD45 isoform and CTLA-4 expression revealed that within 1–2 days after anti-CD45RB treatment, a marked shift in CD45RB expression had already occurred (FIG. 3). This shift persisted at least 10 days after treatment. CTLA-4 expression also underwent a rapid and statistically significant increase. If one compares the percentage of CD45RB$^{Lo}$ cells expressing CTLA-4, it can be seen that after a slight lag, CTLA-4 expression on CD45RB$^{Lo}$ cells was relatively constant for the first week after treatment. However, CTLA-4 expression continued to rise, such that by day 10–12, 30%, and in some animals, 40%, of the CD4+ CD45RBLo cells expressed CTLA-4.

Anti-CD45RB does not induce T Cell activation. To rule out the possibility that the shift in CD45 isoforms and rise in CTLA-4 expression were simply the result of T cell activation by anti-CD45RB (MB23G2), we compared CD4+ splenocytes from treated and untreated animals for expression of the activation markers, CD69, CD25, and CD44 on day 2 and day 6 after treatment (FIG. 4). As seen, anti-CD45RB treatment does not alter expression of molecules that are closely associated with T cell activation and entry into the cell cycle. Moreover, CD45RB and CD44 expression are usually inversely correlated with one another, with CD45RB$^{Hi}$ cells expressing low levels of CD44 and CD45RB$^{Lo}$ cells expressing high levels of CD44[30]. However, after anti-CD45RB treatment, CD44 expression remained bimodal even though over 90% of the cells were CD45RB$^{Lo}$. This shows the relative specificity of the effects of anti-CD45RB and provides further evidence that CD45RB$^{Hi}$ cells are not simply being depleted (which would have removed the CD44$^{Lo}$ population).

Calcineurin Links anti-CD45RB. CTLA-4 and Allograft Survival. The events linking the shift in CD45 isoforms to an upregulation of CTLA-4 expression without overall T cell activation are unknown. To initiate identification of signaling pathways involved in these events, we examined the effects of calcineurin inhibition with the widely used immunosuppressant agent, Cyclosporin A (CsA)[31]. Mice were treated with CsA alone, anti-CD45RB alone, or the combination of these two agents (FIGS. 5a and 5b). Alone, CsA had no effect on CD45RB or on basal CTLA-4 expression. Moreover, CsA-treatment had no effect on anti-CD45RB induced shift in CD45 isoforms (FIG. 5a). In contrast, CsA completely blocked anti-CD45RB-induced upregulation of CTLA-4 (FIGS. 5b and 5c). Thus, only half as many $CD45RB^{Lo}$ cells now expressed CTLA-4.

If upregulation of CTLA-4 expression is critical to the induction of long-term allograft survival by anti-CD45RB, then inhibiting CTLA-4 upregulation should have a detrimental effect on the efficacy of anti-CD45RB treatment. Animals undergoing islet allograft transplantation were treated with either anti-CD45RB or with both anti-CD45RB and CsA (FIG. 5d). The addition of CsA to anti-CD45RB resulted in acute rejection, with a median graft survival of 22 days—identical to that observed when allograft recipients treated with anti-CD45RB also received a mAb blocking CTLA-4 signaling (Table 1).

TABLE 1

Induction of Tolerance By Anti-CD45RB Requires Signals Through CTLA4

| Treatment | | (n) | Graft Survival (d) | Median (d) |
|---|---|---|---|---|
| None | | (5) | 11, 12, 12, 13, 13 | (12) |
| α-CD45RB | (100 ug iv d-1, 0, 5) | (14) | 10, 16, 19, 19, 25, 79, > 120 X8 | (>120)* |
| α-CTLA4 | (200 ug ip d-1, 0, 1) | (5) | 8, 12, 13, 14, 15 | (13) |
| α-CD45RB + α-CTLA4 | (dosed as above) | (9) | 18, 18, 19, 19, 22, 23, 24, 24, 26 | (22) |

Chemically diabetic C57BL/6 recipients of BALB/c islets were untreated (controls) or treated with anti-CD45RB, anti-CTLA-4, or a combination of both mAbs, as described in Methods. Graft Survival of each animal and Median graft survival (in days) is depicted.
*$p < 0.004$ vs all other groups.

Additional Results

Upregulation of CTLA-4 augments CTLA-4-mediated negative signaling in vitro: In soluble form, currently available anti-CTLA-4 antibodies block CTLA-4 signaling. However, co-cross-linking of anti-CTLA-4 with anti-CD3 and anti-CD28 on latex beads can trigger CTLA-4-mediated negative signaling in vitro—resulting in an inhibition of proliferation. The allograft survival data described above demonstrate an important in vivo role for CTLA-4-mediated negative signaling in tolerance induced by anti-CD45RB (MB23G2). To demonstrate that the in vivo upregulation of CTLA-4 also translates into augmented negative signaling through CTLA-4 in vitro, we compared CD4 cells derived from untreated versus anti-CD45RB treated mice for their sensitivity to CTLA-4-mediated inhibition in vitro (FIG. 6). In this assay, CD4 cells from anti-CD45RB treated and untreated mice demonstrated equivalent proliferation after in vitro activation with anti-CD3 and anti-CD28 coated latex beads. When treated with latex beads that also included anti-CTLA-4, CD4 cells from untreated mice exhibited a 20% decrease in proliferation. In contrast, CD4 cells from anti-CD45RB treated mice, which displayed a two-fold upregulation of CTLA-4 expression, were significantly more sensitive to CTLA-4-mediated inhibition, displaying a 3-fold increase in inhibition.

Development of an in vitro model for CTLA-4 upregulation: We next developed an in vitro model to study CTLA-4 upregulation (FIG. 7). Unseparated splenocytes are incubated alone, or in the presence of anti-CD45RB. Compared to the control cells (no anti-CD45RB), CD4 cells incubated with anti-CD45RB exhibit a two-fold increase in CTLA-4 expression within four hours, and this remains stable for at least 24 hours. Similar results were obtained when either purified T cells or CD4 T cells were incubated with anti-CD45RB. As was the case in vitro, anti-CD45RB did not induce the expression of adhesion or activation markers—again indicating a selective effect on CTLA-4 expression.

Comparison of T cell activation-induced and anti-CD45RB-mediated CTLA-4 Expression: Although T cell activation is known to augment CTLA-4 expression, the exact signaling pathways utilized are unknown. Moreover, anti-CD45RB appears to augment CTLA-4 expression without inducing overt T cell activation. To further define the pathways leading to CTLA-4 upregulation after each of these stimuli, we directly compared them in vitro. In contrast to anti-CD45RB-mediated upregulation (described above), T cell activation had no effect on CTLA-4 expression on CD4 cells at 4 hours (FIG. 7). Indeed, T cell activation did not induce a two-fold increase in CTLA-4 expression until 24 hours. When T cell stimulation and anti-CD45RB were combined, additive effects at each time point were seen. Thus, at 4 hours, addition of T cell activation to anti-CD45RB had no additional effect (2 fold increase in CTLA-4). In contrast at 24 hours, CTLA-4 was increased 3–3.5-fold. These results suggest that T cell activation and anti-CD45RB-mediated induction of CTLA-4 are largely independent and lend further support to the notion that CTLA-4 expression can be independently and specifically targeted.

CD45RB-mediated CTLA-4 Expression Requires the NFAT Transcription Factor: Our in vivo data with Cyclosporin A suggested that anti-CD45RB-mediated CTLA-4 upregulation involves calcineurin-mediated signaling pathways. We therefore wished to examine signals lying directly downstream from calcineurin. One main function of calcineurin is to activate the NFAT transcription factor allowing it to translocate from the cytoplasm to its site of action in the cell nucleus. To examine the role of NFAT, we compared anti-CD4RB mediated CTLA-4 expression in CD4 T cells from wild-type mice and those heterozygous for a transgene encoding dominant negative NFAT (DN-NFAT). In contrast to T cells from wild-type mice, anti-CD45RB was unable to augment CTLA-4 expression in T cells from DN-NFAT mice (FIG. 8). However, T cell activation mediated CTLA-4 expression remained intact (at 24 hours) in DN-NFAT mice. These data indicate that anti-CD45RB-mediated CTLA-4 expression, but not that mediated by T cell activation, requires intact NFAT. Such studies provide yet additional evidence that CTLA-4 can be specifically targeted and moreover, begin to identify pathways/molecules that might be targeted for therapeutic purposes.

Discussion

Although the biochemical mechanisms remain unresolved, CTLA-4-derived signals are crucial for the regulation of peripheral tolerance[3,32]. Unfortunately, no CTLA-4 agonist has been identified and until now, there has been no known therapeutic means to utilize this negative regulator to promote peripheral tolerance in vivo. Here we demonstrate that CTLA-4 expression can be upregulated without overt T cell activation, allowing this potent inhibitory pathway to be harnessed for the induction of long-term allograft survival. While not wishing to be bound to any theory, we hypothesize that anti-CD45RB acts through an entirely novel means: The rapid shift towards the lower Mr CD45 isoforms primes CD4 cells for CTLA-4 expression. By the time host antigen presenting cells have upregulated their CD80 and CD86 costimulatory ligands, potentially alloreactive CD4 cells either express, or have the capacity to rapidly express CTLA-4 and are subject to downregulation. In this regard, $CD45RB^{Lo}$ cells not only express CTLA-4, but have been shown to be more sensitive than $CD45RB^{Hi}$ cells to CTLA-4-mediated inhibition in vitro[28]. In addition to demonstrating an important in vivo role for CTLA-4 in anti-CD45RB mediated allograft survival, we have also observed that CD4 cells from anti-CD45RB treated animals exhibit increased sensitivity to inhibition through CTLA-4 signalling in vitro.

Recent studies suggest that a CD4+ CD25+ population that contains cells that constitutively express CTLA-4 can play an important role in regulating autoimmunity[7,33,34]. In one report, these regulatory cells also expressed the lower Mr CD45 isoforms[33]. Interestingly, CTLA-4 ligation appears to augment inhibitory activity by these cells, suggesting another means by which CTLA-4 can downmodulate the immune system. The relationship between these regulatory cells and the CTLA-4+ cells induced by anti-CD45RB treatment is unclear. However, we did not detect any increase in CD25 expression on CD4 cells in anti-CD45RB treated animals. Regardless, it is entirely possible that cells expressing de novo CTLA-4 after anti-CD45RB treatment act to downregulate allo- or autoimmune responsiveness.

The regulation of CTLA-4 expression is complex and occurs at multiple levels. Both CTLA-4 transcription and mRNA stability are upregulated by T cell activation[11,35]. Maximal protein expression is seen 48–72 hours later, and in previous studies, it appears to require entry into the cell cycle[10,11]. Although CTLA-4 expression is largely intracellular, TCR ligation induces rapid movement from endosomes to the plasma membrane, its site of action and ligand binding[9,10]. Nonetheless, CTLA-4 is quickly endocytosed, precluding significant accumulation on the surface at physiologic temperatures[10]. Surface expression and endocytosis are highly regulated through reversible tyrosine phosphorylation of the cytoplasmic tail which inhibits interaction with the AP-2 adaptor protein, thereby promoting surface expression[36,29]. Moreover, intracytoplasmic levels of CTLA-4 may also be regulated by interaction with AP-1, which targets CTLA-4 to lysosomal compartments for degradation[37].

The signaling pathways leading from T cell activation to CTLA-4 transcription are not well-defined. Basal transcription is extremely low and optimal induction requires stimulation through both the TCR and CD28[11,35]. Analysis of a 335 bp upstream regulatory region of the CTLA-4 promoter reveals potential binding sites for NFAT, AP-1, NFκB, and a number of other transcription factors[35]. Although actual binding of these factors to the CTLA-4 promoter has not been confirmed, CsA inhibits activation-induced CTLA-4 expression[10,11], suggesting regulation by NFAT or other calcineurin-regulated transcription factors. However, these studies cannot exclude an indirect effect of CsA, mediated by blockade of cell cycle progression[10]. In contrast to activation-induced CTLA-4 expression, essentially nothing is known about the regulation of basal expression. Moreover, the notion that CTLA-4 expression can be augmented short of full-scale T cell activation, is entirely new. In this regard, we have shown that certain anti-CD45RB monoclonal antibodies not only augment CTLA-4 expression without overt T cell activation, but do so through pathways that are at least partially independent from those used by the T cell receptor. We now demonstrate that anti-CD45RB treatment augments constitutive expression of intracellular CTLA-4 on CD4 cells. This CTLA-4 appears to undergo normal regulation of surface expression and endocytosis, and exhibits ready access to the cell surface upon T cell activation. Although anti-CD45RB could raise intracellular CTLA-4 expression by reducing AP-1-mediated shuttling of CTLA-4 to the lysosomes, complete inhibition by CsA suggests primary regulation at the level of transcription. This is strongly supported by our studies showing requisite involvement of the NFAT transcription factor. While NFAT is also upregulated by T cell receptor ligation and may contribute to the activation-induced increase in CTLA-4 expression, it is not essential. These data, along with the kinetic differences, provide further evidence that T cell receptor ligation and anti-CD45RB-mediated signals are partially distinct, thus allowing CTLA-4 to be specifically targeted. Further identification of the discrete signals involved are likely to identify new pharmacological targets.

The interaction between CD45 and CTLA-4, and indeed their connection through calcineurin, was completely unanticipated. Nonetheless, potential interactions between CD45 and the calcineurin pathway have been reported previously. Co-crosslinking CD45 and CD3, and dimerization of EGFR-CD45 chimeras has been shown to disrupt $Ca^{+2}$ flux[42,43]. Interestingly, the anti-CD45RB mAb MB23G2 used in this report, has been shown to augment anti-CD3-induced tyrosine phosphorylation of PLCg1 in a T cell hybridoma[27]. However, in preliminary studies, we have been unable to demonstrate that anti-CD45RB (MB23G2) alone, or cross-linked by anti-rat Ig, increases intracellular $Ca^{+2}$. Moreover, it should be emphasized that not all antibodies targeting CD45, or CD45RB, have the capacity to upregulate CTLA-4.

Our findings suggest that ligation of CD45 with anti-CD45RB alters signaling through calcineurin and NFAT, and this specifically upregulates CTLA-4 expression. We show that CTLA-4 expression can be induced without overt T cell activation. This provides a practical means of harnessing this downregulatory pathway for the induction of long-term allograft survival. Screening for agents that act through aumentation of CTLA-4 is likely to produce drugs that of great benefit in treating and preventing transplant rejection and other immune-mediated diseases.

REFERENCES

1. Tivol, E. et al. Loss of CTLA-4 leads to massive lymphoproliferation and fatal multiorgan tissue destruction, revealing a critical negative regulatory role of CTLA-4. *Immunity* 3, 541–547 (1995).
2. Waterhouse P., Penninger, J. M., Timms E., Wakeham A., Shahinian A., Lee K. P., Thompson C. B., Griesser, H., & Mak T. W. Lymphoproliferative disorders with early lethality in mice deficient in Ctla-4. *Science* 270, 985–988 (1995).
3. Perez, V. L. et al. Induction of peripheral T cell tolerance in vivo requires CTLA-4 engagement. *Immunity* 6, 411–417 (1997).
4. Leach, D. R., Krummel, M. F. & Allison, J. P. Enhancement of antitumor immunity by CTLA-4 blockade. *Science* 271, 1734–1736 (1996).
5. Luhder, F., Hoglund, P., Allison, J. P., Benoist, C. & Mathis, D. Cytotoxic T lymphocyte-associated antigen 4 (CTLA-4) regulates the unfolding of autoimmune diabetes. *J. Exp. Med.* 187, 427–432 (1998).

6. Karandikar, N. J., Vanderlugt, C. L., Walunas, T. L., Miller, S. D. & Bluestone, J. A. CTLA-4: a negative regulator of autoimmune disease. *J. Exp. Med.* 184, 783–788 (1996).
7. Takahashi, T. et al. Immunologic self-tolerance maintained by CD25(+)CD4(+) regulatory T cells constitutively expressing cytotoxic T lymphocyte-associated antigen 4. *J. Exp. Med.* 192, 303–310 (2000).
8. Judge, T. A. et al. The role of CD80, CD86, and CTLA4 in alloimmune responses and the induction of long-term allograft survival. *J. Immunol.* 162, 1947–1951 (1999).
9. Linsley, P. S. et al. Intracellular trafficking of CTLA-4 and focal localization towards sites of TCR engagement. *Immunity* 4, 535–543 (1996).
10. Alegre, M. L. et al. Regulation of surface and intracellular expression of CTLA4 on mouse T cells. *J. Immunol.* 157, 4762–4770 (1996).
11. Finn, P. W. et al. Synergistic induction of CTLA-4 expression by costimulation with TCR plus CD28 signals mediated by increased transcription and messenger ribonucleic acid stability. *J. Immunol.* 158, 4074–4081 (1997).
12. Krummel, M. F. & Allison, J. P. CD28 and CTLA-4 have opposing effects on the response of T cells to stimulation. *J. Exp. Med.* 182, 459–465 (1995).
13. Walunas, T. L. et al. CTLA-4 can function as a negative regulator of T cell activation. *Immunity* 1, 405–413 (1994).
14. Trowbridge, I. S. & Thomas, M. L. CD45: an emerging role as a protein tyrosine phosphatase required for lymphocyte activation and development. *Ann. Rev. Immunol.* 12, 85–116 (1994).
15. Kashio, N., Matsumoto, W., Parker, S. & Rothstein, D. M. The second domain of the CD45 transmembrane protein tyrosine phosphatase is critical for IL-2 secretion and for recruitment of substrates in vivo. *J. Biol. Chem.* 273, 33856–33863 (1998).
16. Bottomly, K. et al. A monoclonal antibody to murine CD45R distinguishes CD4 T cell populations that produce different cytokines. *Eur. J. Immunol.* 19, 617–623 (1989).
17. Lee, W., Yin, X.-M. & Vitetta, E. Functional and ontogenetic analysis of murine CD45hi and CD45lo CD4+ T cells. *J. Immunol.* 144, 3288–3295 (1990).
18. Powrie, F. et al. Inhibition of Th1 response prevents inflammatory bowel disease in scid mice reconstituted with CD45RBhi CD4+ T cells. *Immunity* 1, 553–562 (1994).
19. Morimoto, C., Letvin, N. L., Distaso, J. A., Aldrich. W. R. & Schlossman, S.
F. The isolation and characterization of the human suppressor inducer T cell subset. *J. Immunol.* 134, 1508–1515 (1985).
20. Rothstein, D. M., Yamada, A., Schlossman, S. F. & Morimoto, C. Cyclic regulation of CD45 isoform expression in a long-term human CD4+ CD45RA+ T cell line. *J. Immunol.* 146, 1175–1183 (1991).
21. Sparshott, S. & Bell, E. Membrane CD45R isoform exchange on CD4 T cells is rapid, frequent and dynamic in vivo. *Eur. J. Immunol.* 24, 2573–2578 (1994).
22. Michie, C. A., McLean, A., Alcock, C. & Beverley, P. C. L. Lifespan of human lymphocyte subsets defined by CD45 isoforms. *Nature* 360, 264–265 (1992).
23. McKenney, D. W., Onodera, H., Gorman, L., Mimura, T. & Rothstein, D. M. Individual isoforms of the CD45 protein tyrosine phosphatase differentially regulate IL-2 secretion and activation signal pathways involving Vav in T cells. *J. Biol. Chem.* 270, 24949–24954 (1995).
24. Onodera, H., Motto, D. G., Koretzky, G. A. & Rothstein, D. M. Differential Regulation of Activation-Induced Tyrosine Phosphorylation and Recruitment of SLP-76 to Vav by Distinct Isoforms of the CD45 Protein Tyrosine Phosphatase. *J. Biol. Chem.* 271, 2225–2230 (1996).
25. Novak, T. et al. Isoforms of the transmembrane tyrosine phosphatase CD45 differentially affect T cell recognition. *Immunity* 1, 109–119 (1994).
26. Basadonna, G. et al. Antibody mediated targeting of CD45 isoforms: A novel immunotherapeutic strategy. *Proc. Nat. Acad. Sci. USA.* 95, 3821–3826 (1998).
27. Lazarovits, A. et al. Prevention and reversal of renal allograft rejection by antibody against CD45RB. *Nature* 380, 717–720 (1996).
28. Metz, D. P., Farber, D. L., Taylor, T. & Bottomly, K. Differential role of CTLA-4 in regulation of resting memory versus naive CD4 T cell activation. *J. Immunol.* 161, 5855–5861 (1998).
29. Chuang, E. et al. Interaction of CTLA-4 with the clathrin-associated protein AP50 results in ligand-independent endocytosis that limits cell surface expression. *J. Immunol.* 159, 144–151 (1997).
30. Croft, M., Duncan, D. D. & Swain, S. L. Response of naive antigen-specific CD4+ T cells in vitro: characteristics and antigen-presenting cell requirements. *J. Exp. Med.* 176, 1431–1437 (1992).
31. Liu, J. et al. Calcineurin is a common target of cyclophilin-cyclosporin A and FKBP-FK506 complexes. *Cell* 66, 807–815 (1991).
32. Walunas, T. L. & Bluestone, J. A. CTLA-4 regulates tolerance induction and T cell differentiation in vivo. *J. Immunol.* 160, 3855–3860 (1998).
33. Read, S., Malmstrom, V. & Powrie, F. Cytotoxic T lymphocyte-associated antigen 4 plays an essential role in the function of CD25(+)CD4(+) regulatory cells that control intestinal inflammation. *J. Exp. Med.* 192, 295–302 (2000).
34. Salomon, B. et al. B7/CD28 costimulation is essential for the homeostasis of the CD4+ CD25+ immunoregulatory T cells that control autoimmune diabetes. *Immunity* 12, 431–440 (2000).
35. Perkins, D. et al. Regulation of CTLA-4 expression during T cell activation. *J. Immunol.* 156, 4154–4159 (1996).
36. Shiratori, T. et al. Tyrosine phosphorylation controls internalization of CTLA-4 by regulating its interaction with clathrin-associated adaptor complex AP-2. *Immunity* 6, 583–589 (1997).
37. Schneider, H. et al. Cytolytic T lymphocyte-associated antigen-4 and the TCR zeta/CD3 complex, but not CD28, interact with clathrin adaptor complexes AP-1 and AP-2. *J. Immunol.* 163, 1868–1879 (1999).
38. Rothstein, D. M., Saito, H., Streuli, M., Schlossman, S. F. & Morimoto, C. The alternative splicing of the CD45 tyrosine phosphatase is controlled by negative regulatory trans-acting splicing factors. *J. Biol. Chem.* 267, 7139–7147 (1992).
39. Tedder, T. F., Clement, L. T. & Cooper, M. D. Human lymphocyte differentiation antigens HB-10 and HB-11 I. Ontogeny of antigen expression. *J. Immunol.* 134, 2983–2988 (1985).
40. Bell, E. B. & Sparshott, S. M. Interconversion of CD45R subsets of CD4 T cell in vivo. *Nature* 348, 163–166 (1990).
41. Leitenberg, D., Novak, T., Farber, D. L., Smith, B. R. & Bottomly, K. The extracellular domain of CD45 controls association with the CD4/T cell receptor complex and the response to antigen specific stimulation. *J. Exp. Med.* 183, 249–259 (1996).
42. Leitenberg, D., Constant, S., Lu, D. D., Smith, B. R. & Bottomly, K. CD4 and CD45 regulate qualitatively distinct patterns of calcium mobilization in individual CD4+ T cells. *Eur. J. Immunol.* 25, 2445–2451 (1995).
43. Desai, D., Sap, J., Schlessinger, J. & Weiss, A. Ligand-mediated negative regulation of a chimeric transmembrane receptor tyrosine phosphatase. *Cell* 73, 541–554 (1993).
44. Li, Y. et al. Blocking both signal 1 and signal 2 of T-cell activation prevents apoptosis of alloreactive T cells and induction of peripheral allograft tolerance. *Nat. Med.* 5, 1298–1302 (1999).

The papers and patents cited above and in the text of the specification are expressly incorporated herein in their entireties by reference.

The above description is for the purpose of teaching a person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed steps in any sequence which is effective to meet the objectives there intended, unless the context specifically indicates the contrary.

What is claimed is:

1. A method for screening for an agent useful in promoting immunosuppression or immunologic tolerance in a mammal comprising:
    (a) administering a test agent to an experimental animal;
    (b) obtaining a biological sample comprising T-cells from the animal and a sample from a control animal of the same species;
    (c) examining CTLA-4 expression on both the T-cells obtained from the experimental animal to which the test agent has been administered and the T-cells obtained from the control animal, by measuring the levels of at least one of cell surface CTLA-4, cytoplasmic CTLA-4, or CTLA-4 mRNA in the T-cells, and comparing the levels of CTLA-4 on the T-cells in the control and experimental animals;
    (d) examining T-cell activation by measuring T-cell activation in the T-cells obtained from the experimental animal to which the test agent has been administered, by measuring upregulation of T-cell markers, T-cell proliferation, and entry of T-cells into cell cycle; and
    (e) identifying whether the administered test agent can be used to promote immunosuppression or immunologic tolerance in a mammal by determining if the administered test agent increases levels of CTLA-4 on T-cells in the sample from the experimental animal as compared to the levels of CTLA-4 on T-cells in the control animal sample;
    wherein the increase of CTLA-4 on the T-cells in the experimental sample occurs without observing T-cell activation.

2. A method according to claim 1 wherein an immunoassay is employed to determine the levels of CTLA-4 in the samples.

3. A method according to claim 2 which employs polyclonal, monoclonal or fusion phage antibodies to CTLA-4.

4. A method according to claim 1 wherein protein analysis is used to determine the levels of CTLA-4 in the samples.

5. A method according to claim 1 wherein the biological sample comprises cells that are fixed, permeabilized, and incubated with an anti-CTLA-4 tagged antibody prior to comparison.

6. A method according to claim 1 wherein the animals are mice or non-human primates.

7. A method for screening for an agent useful in promoting immunosuppression or immunologic tolerance in a mammal comprising:
    (a) adding a test agent to a culture of mammalian cells comprising T-cells;
    (b) measuring the levels of at least one of cell surface CTLA-4, cytoplasmic CTLA-4, or CTLA-4 mRNA in the T-cells in the culture of mammalian cells to which the test agent has been added and in T-cells in an untreated culture of mammalian cells comprising T-cells used as a control, and comparing the two;
    (c) examining T-cell activation by measuring T-cell activation in the culture of mammalian cells comprising T-cells to which the test agent has been added, by measuring upregulation of T-cell markers, T-cell proliferation, and entry of T-cells into cell cycle, and
    (d) identifying whether the administered test agent can be used to promote immunosuppression or immunologic tolerance in a mammal, by determining if the administered test agent increases levels of CTLA-4 on T-cells in the culture of mammalian cells to which the test agent has been added as compared to the levels of CTLA-4 on T-cells in the untreated culture of mammalian cells;
    wherein the increase of CTLA-4 on T-cells in the culture of mammalian cells to which the test agent has been added occurs without observing T-cell activation.

8. A method according to claim 7 wherein an immunoassay is employed to determine the levels of CTLA-4 in the samples.

9. A method according to claim 8 which employs polyclonal, monoclonal or fusion phage antibodies to CTLA-4.

10. A method according to claim 7 wherein protein analysis is used to determine the levels of CTLA-4 in the samples.

11. A method according to claim 7 where the cells are fixed, permeabilized, and incubated with anti-CTLA-4 tagged antibody prior to comparison.

12. A method according to claim 7 where the cells are derived from mice, non-human primates, or human subjects.

* * * * *